US009980835B2

(12) United States Patent
Pazienza et al.

(10) Patent No.: US 9,980,835 B2
(45) Date of Patent: May 29, 2018

(54) MEDICAL DEVICE FOR IMPLANTATION INTO LUMINAL STRUCTURES INCORPORATING CORRUGATED STRUCTURAL ELEMENTS

(71) Applicant: OrbusNeich Medical, Inc., Ft. Lauderdale, FL (US)

(72) Inventors: John Pazienza, Pompano Beach, FL (US); Robert J Cottone, Davie, FL (US); Jennifer Ippolito, Plantation, FL (US); Mohamad Ike Juman, Davie, FL (US); Dennis Liong, Ft. Lauderdale, FL (US)

(73) Assignee: ORBUSNEICH MEDICAL INC., Fort Lauderdale, FL (US)

( * ) Notice: Subject to any disclaimer, the term of this patent is extended or adjusted under 35 U.S.C. 154(b) by 449 days.

(21) Appl. No.: 14/521,324

(22) Filed: Oct. 22, 2014

(65) Prior Publication Data
US 2015/0112422 A1 Apr. 23, 2015

Related U.S. Application Data

(63) Continuation of application No. 14/060,012, filed on Oct. 22, 2013.
(Continued)

(51) Int. Cl.
*A61F 2/915* (2013.01)

(52) U.S. Cl.
CPC .... *A61F 2/915* (2013.01); *A61F 2002/91541* (2013.01); *A61F 2002/91558* (2013.01);
(Continued)

(58) Field of Classification Search
CPC .... A61F 2002/9154; A61F 2002/91558; A61F 2210/0004; A61F 2250/0096; A61F 2/915;
(Continued)

(56) References Cited

U.S. PATENT DOCUMENTS 5,697,971 A 12/1997 Fischell et al.
5,843,175 A * 12/1998 Frantzen ............... A61F 2/91
623/1.15
(Continued)

FOREIGN PATENT DOCUMENTS

CN 1479596 A 3/2004
EP 1093771 A2 4/2001
(Continued)

OTHER PUBLICATIONS

International Search Report and Written Opinion for International Patent Application No. PCT/US2013/066128 dated Apr. 25, 2014. 11 pages.
(Continued)

*Primary Examiner* — Thomas J Sweet
*Assistant Examiner* — Seema Mathew
(74) *Attorney, Agent, or Firm* — Leason Ellis LLP

(57) ABSTRACT

Expandable scaffolds or stents include circumferential elements having a corrugated pattern, which can include a plurality of linear or nonlinear segments. The corrugated pattern distributes stress more uniformly along the circumferential elements, improves radial strength of the scaffolds, reduces acute recoil after deployment, and reduces creep. The scaffolds can be made from a bioabsorbable material.

32 Claims, 35 Drawing Sheets

Related U.S. Application Data

(60) Provisional application No. 61/895,957, filed on Oct. 25, 2013, provisional application No. 61/968,025, filed on Mar. 20, 2014.

(52) U.S. Cl.
CPC ............... *A61F 2210/0004* (2013.01); *A61F 2250/0096* (2013.01)

(58) Field of Classification Search
CPC .... A61F 2/88; A61F 2/885; A61F 2/89; A61F 2/90; A61F 2/91; A61F 2002/9155
See application file for complete search history.

(56) References Cited

U.S. PATENT DOCUMENTS

| | | | | |
|---|---|---|---|---|
| 6,013,854 A * | 1/2000 | Moriuchi | ............... | A61F 2/91 606/194 |
| 6,066,169 A * | 5/2000 | McGuinness | ............. | A61F 2/91 623/1.16 |
| 6,656,220 B1 * | 12/2003 | Gomez | ............... | A61F 2/91 623/1.15 |
| 6,749,629 B1 * | 6/2004 | Hong | ............... | A61F 2/91 623/1.15 |
| 7,090,694 B1 * | 8/2006 | Morris | ............... | A61F 2/856 623/1.15 |
| 7,175,654 B2 | 2/2007 | Bonsignore et al. | | |
| 7,867,273 B2 | 1/2011 | Pappas et al. | | |
| 7,967,852 B2 | 6/2011 | Addonizio et al. | | |
| 2001/0044649 A1 | 11/2001 | Vallana et al. | | |
| 2002/0045935 A1 * | 4/2002 | Jang | ............... | A61F 2/91 623/1.16 |
| 2002/0058990 A1 * | 5/2002 | Jang | ............... | A61F 2/91 623/1.15 |
| 2003/0014102 A1 * | 1/2003 | Hong | ............... | A61F 2/91 623/1.15 |
| 2003/0033003 A1 | 2/2003 | Harrison et al. | | |
| 2003/0093144 A1 * | 5/2003 | Jang | ............... | A61F 2/91 623/1.15 |
| 2003/0149474 A1 * | 8/2003 | Becker | ............... | A61F 2/91 623/1.15 |
| 2004/0002753 A1 * | 1/2004 | Burgermeister | ............... | A61F 2/91 623/1.15 |
| 2004/0133265 A1 * | 7/2004 | Duffy | ............... | A61F 2/91 623/1.16 |
| 2005/0080479 A1 * | 4/2005 | Feng | ............... | A61F 2/91 623/1.15 |
| 2006/0276880 A1 * | 12/2006 | Neuss | ............... | A61F 2/91 623/1.15 |
| 2007/0156230 A1 | 7/2007 | Dugan et al. | | |
| 2007/0255391 A1 * | 11/2007 | Hojeibane | ............... | A61F 2/91 623/1.15 |
| 2008/0051868 A1 * | 2/2008 | Cottone | ............... | A61F 2/91 623/1.11 |
| 2008/0051873 A1 * | 2/2008 | Cottone | ............... | A61F 2/91 623/1.16 |
| 2008/0097575 A1 | 4/2008 | Cottone | | |
| 2008/0255655 A1 * | 10/2008 | Kusleika | ............... | A61F 2/91 623/1.11 |
| 2008/0294239 A1 | 11/2008 | Casey | | |
| 2009/0036964 A1 * | 2/2009 | Heringes | ............... | A61F 2/91 623/1.2 |
| 2009/0182404 A1 | 7/2009 | Shokoohi | | |
| 2009/0240317 A1 | 9/2009 | Cottone et al. | | |
| 2010/0004725 A1 * | 1/2010 | Zipse | ............... | A61F 2/91 623/1.2 |
| 2010/0131044 A1 | 5/2010 | Patel | | |
| 2011/0029064 A1 | 2/2011 | Burpee et al. | | |
| 2011/0125251 A1 | 5/2011 | Cottone et al. | | |
| 2011/0130822 A1 * | 6/2011 | Cottone | ............... | A61F 2/91 623/1.15 |
| 2011/0238156 A1 | 9/2011 | Tischler et al. | | |
| 2011/0238157 A1 * | 9/2011 | Li | ............... | A61F 2/91 623/1.16 |
| 2011/0313508 A1 | 12/2011 | Kolachalama et al. | | |
| 2012/0016458 A1 | 1/2012 | Abunassar | | |
| 2012/0172972 A1 * | 7/2012 | Meyer | ............... | A61F 2/915 623/1.16 |
| 2012/0220934 A1 | 8/2012 | Diener et al. | | |
| 2013/0085563 A1 * | 4/2013 | Stankus | ............... | A61L 31/041 623/1.15 |
| 2013/0238078 A1 | 9/2013 | Sudhir et al. | | |
| 2013/0261733 A1 | 10/2013 | Su | | |
| 2013/0268054 A1 | 10/2013 | Cottone et al. | | |
| 2016/0213499 A1 * | 7/2016 | Zheng | ............... | A61F 2/915 |

FOREIGN PATENT DOCUMENTS

| | | |
|---|---|---|
| WO | 2003017870 A1 | 3/2003 |
| WO | 2009080327 | 7/2009 |
| WO | 2012103527 A1 | 8/2012 |

OTHER PUBLICATIONS

International Search Report and Written Opinion for International Patent Application No. PCT/US2014/061831 dated Mar. 31, 2015. 12 pages.

Supplementary European Search Report and Written Opinion for European Patent Application No. 14855847.1 dated May 12, 2017. 7 pages.

* cited by examiner

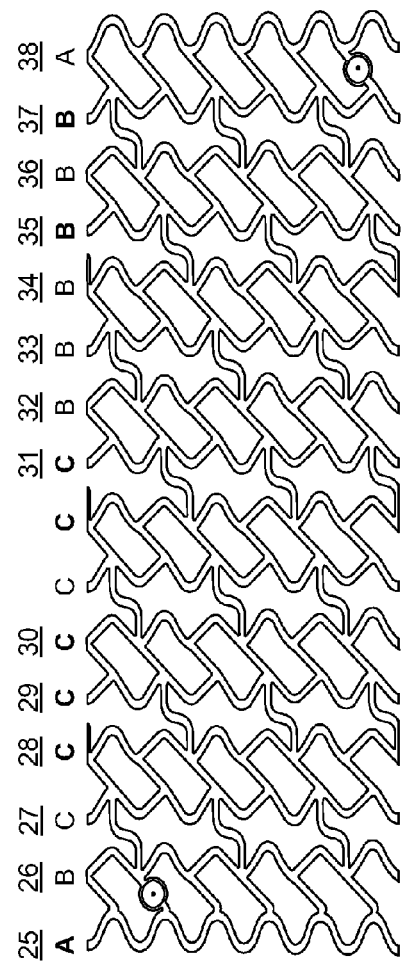
FIG. 2A
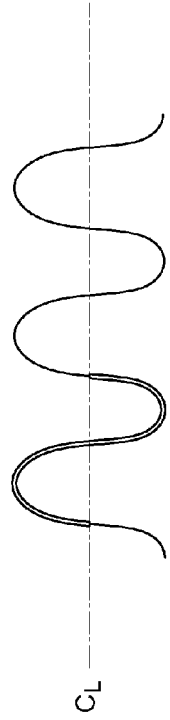
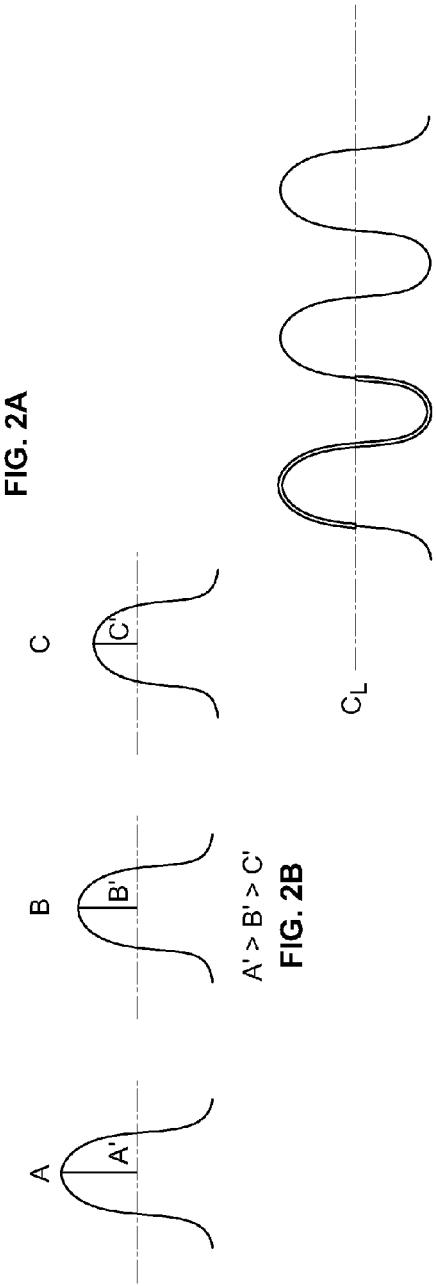
$A' > B' > C'$
FIG. 2B
FIG. 2C

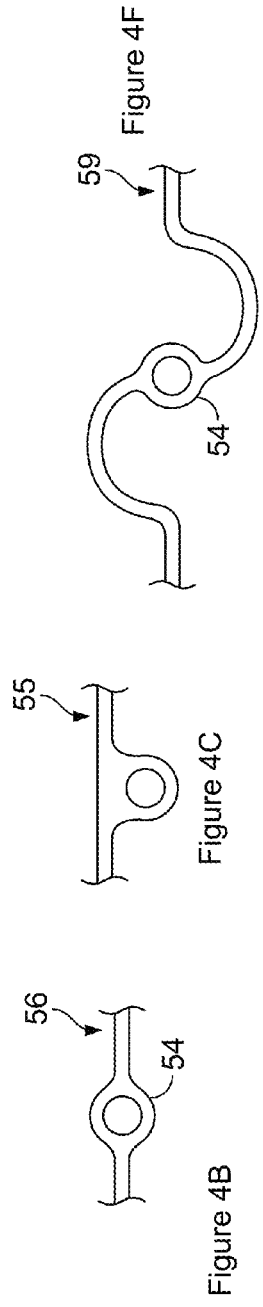

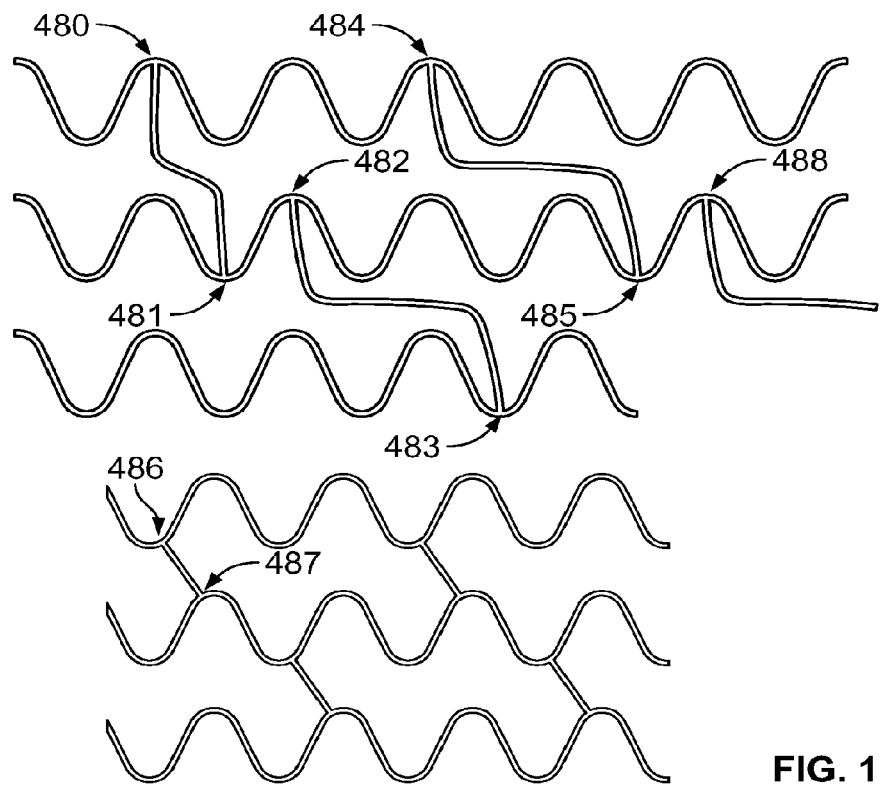
FIG. 14C
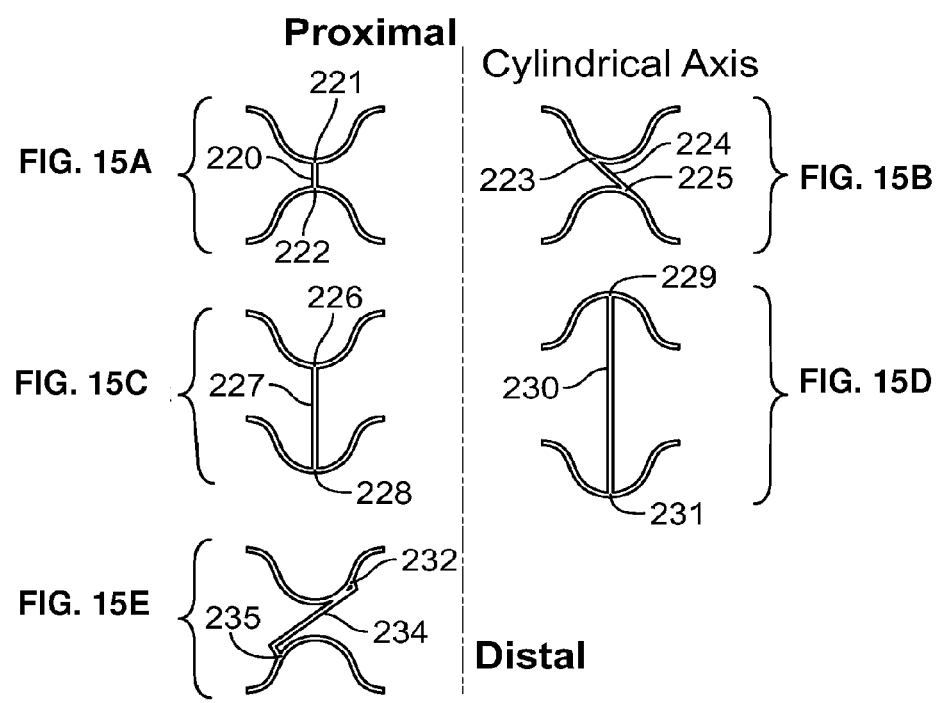

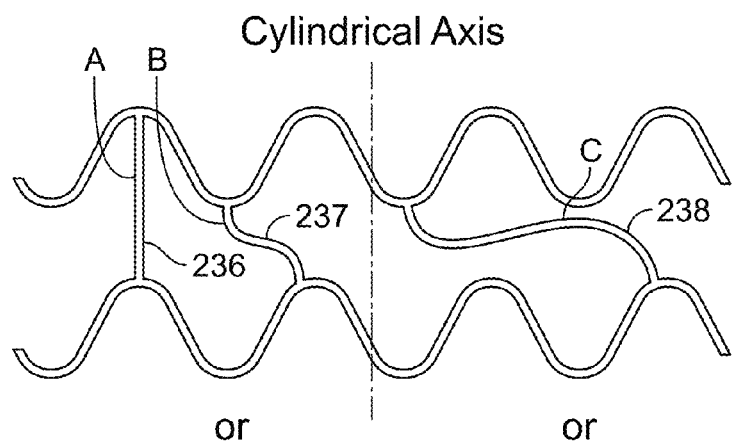
FIG. 16
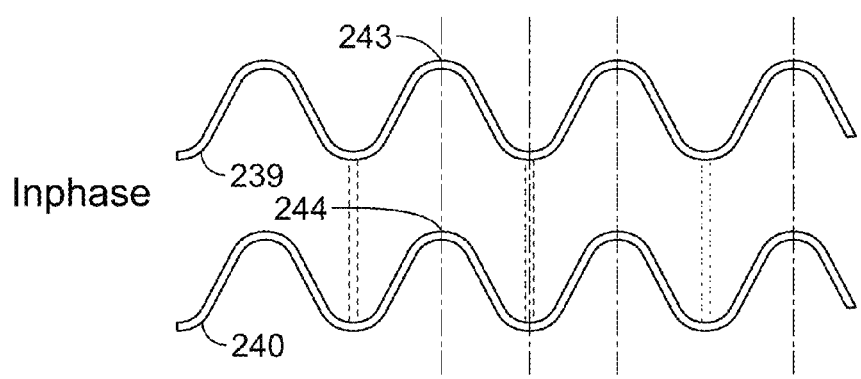
FIG. 17A1
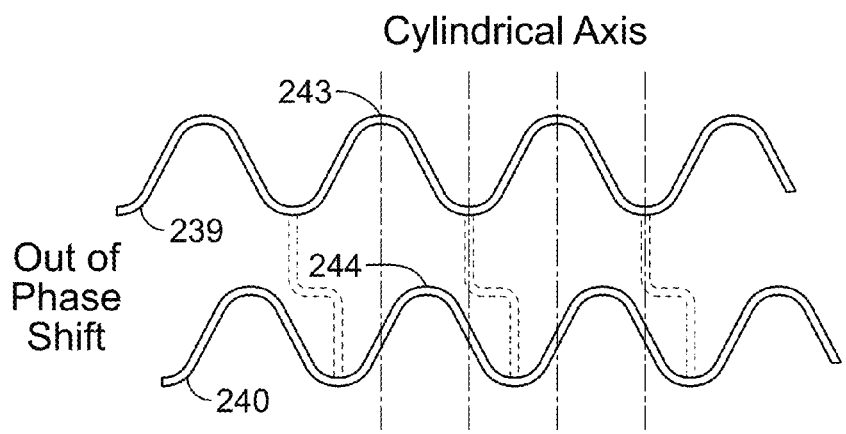
FIG. 17A2

MEDICAL DEVICE FOR IMPLANTATION INTO LUMINAL STRUCTURES INCORPORATING CORRUGATED STRUCTURAL ELEMENTS

CROSS REFERENCE TO RELATED APPLICATION

This application is a continuation-in-part of U.S. application Ser. No. 14/060,012, filed Oct. 22, 2013, and claims priority to U.S. provisional application No. 61/895,957, filed Oct. 25, 2013, and U.S. provisional application No. 61/968,025, filed Mar. 20, 2014. The content of each of these prior-filed applications is incorporated herein by reference in its entirety.

FIELD OF THE INVENTION

The present invention relates to stents. In particular, the present invention relates to geometric designs of stents which exhibit a high degree of radial strength and flexibility and which can be formed from bioabsorbable polymers.

BACKGROUND OF THE INVENTION

Stents are vascular scaffolds that are positioned in diseased vessel segments to support the vessel walls. During angioplasty, stents are used to repair and reconstruct blood vessels. Placement of a stent in the affected arterial segment prevents elastic recoil and closing of the artery. Stents also prevent local dissection of the artery along the medial layer. Physiologically, stents may be placed inside the lumen of any space, such as an artery, vein, bile duct, urinary tract, alimentary tract, tracheobronchial tree, cerebral aqueduct or genitourinary system. Stents may also be placed inside the lumen of non-human animals, such as primates, horses, cows, pigs and sheep.

In general, there are two types of vascular scaffolds or stents: self-expanding and balloon-expandable. Self-expanding stents automatically expand once they are released and assume a deployed, expanded state. A self-expanding stent is placed in the vessel by inserting the stent in a compressed state into the affected region, e.g., an area of stenosis. Compression or crimping of the stent can be achieved using crimping equipment (see, http://www.machinesolutions.org/stent_crimping.htm, April, 2009). The stent may also be compressed using a tube that has a smaller outside diameter than the inner diameter of the affected vessel region. Once the compressive force is removed or the temperature raised, the stent expands to fill the lumen of the vessel. When the stent is released from confinement in the tube, the stent expands to resume its original shape, in the process becoming securely fixed inside the vessel against the wall.

A balloon-expandable stent is expanded using an inflatable balloon catheter. Balloon-expandable stents may be implanted by mounting the stent in an unexpanded or crimped state on a balloon segment of a catheter. The catheter, after having the crimped stent placed on it, is inserted through a puncture in a vessel wall and moved through the vessel until it is positioned in the portion of the vessel that is in need of repair. The stent is then expanded by inflating the balloon catheter against the inside wall of the vessel. Specifically, the stent is plastically deformed by inflating the balloon so that the diameter of the stent is increased and the stent expanded.

There are limitations common to many stents. For example, stents whose bodies are made from polymeric material often suffer from excessive recoil and low radial strength. There is a need for improved stent design that addresses these problems.

SUMMARY OF THE INVENTION

In one aspect, the present invention provides an expandable scaffold, e.g., a stent, for implanting in a body lumen. The scaffold has a compressed or crimped state and an expanded state, and includes a plurality of circumferential elements each having a plurality of undulations in the form of alternating peaks and valleys, the plurality of circumferential elements forming a generally cylindrical shape having a longitudinal (or cylindrical) axis. The plurality of circumferential elements comprise a first circumferential element, a second circumferential element, and a third circumferential element. The first and second circumferential elements are longitudinally adjacent, the second and third circumferential elements are longitudinally adjacent. The first and second circumferential elements are connected by a plurality of first connection elements; the second and third circumferential elements are connected by a plurality of second connection elements. At least one of the circumferential elements comprises at least one undulation comprising a corrugated pattern. The corrugated pattern can include at least six linear segments (e.g., 6-64 linear segments, 6-36 linear segments, etc.) serially connected to one another, each of the at least six linear segments being not collinear with an adjacent connected linear segment when the scaffold is in an expanded state. The connected linear segments can approximate a period of a sinusoidal wave when the scaffold is in an expanded state. The length of each of the connected linear segments can be the same or vary from each other. The corrugated pattern can also include curvilinear segments. The corrugated pattern can be adopted for an entire circumferential element, and/or all of the circumferential elements in a scaffold.

In one embodiment, the scaffold can comprise bioabsorbable polymeric material, such as poly-L-lactide (PLLA). In another embodiment, the scaffold comprises a biocorrodable metal.

The plurality of first (or second) connection elements can comprise at least two connection elements, e.g., three first (or second) connection elements. The first connection elements can be linear or curvilinear, e.g., S or Z-shaped. A marker dot can be included in a first or second connection element.

In one embodiment, the scaffold includes a marker dot. The marker dot can be incorporated into or attached to a connection element. The marker dot can have a cup-like configuration having a mouth and a bottom, and can include a hole in the bottom of the cup.

In one embodiment of the scaffold, the peaks and valleys of the first circumferential element are substantially in-phase with the peaks and valleys of the second circumferential element. Each of the first connection elements connects a valley of the first circumferential element with a peak of the second circumferential element, the peak being adjacent to a valley of the second circumferential element that is longitudinally aligned with the valley of the first circumferential element. In a further embodiment, the peaks and valleys of the second circumferential element are substantially in-phase with the peaks and valleys of the third circumferential element, and each of the second connection elements connects, on one side, to a peak of the second circumferential element which is connected to the first circumferential element by a first connection element, and on the other side, to a valley of the third circumferential element adjacent to a peak of the third circumferential element that is longitudinally aligned with the peak of the second circumferential element. In other embodiments, each of the second connection elements connects, on one side, to a valley of the second circumferential element adjacent to the peak of the second circumferential element that is connected to the first circumferential element by a first connection element, and on the other side, to a peak of the third circumferential element which is adjacent to a valley of the third circumferential element being longitudinally aligned with the valley of the second circumferential element, and each of the first connection elements is not longitudinally aligned with any of the second connection elements.

In one embodiment of the scaffold, the peaks and valleys of the first circumferential element are substantially in-phase with the peaks and valleys of the second circumferential element, and each of the first connection elements connects a peak of the first circumferential element with a peak of the second circumferential element that is longitudinally aligned with the peak of the first circumferential element. In a further embodiment, the peaks and valleys of the second circumferential element are substantially in-phase with the peaks and valleys of the third circumferential element. Each of the second connection elements connects, on one side, to a valley of the second circumferential element that is adjacent to the peak connected with the first connection element, and on the other side, to a valley of the third circumferential element being longitudinally aligned with the valley of the second circumferential element. In another embodiment, the peaks and valleys of the second circumferential element are substantially in-phase with the peaks and valleys of the third circumferential element, and each of the second connection elements connects, on one side, to a peak of the second circumferential element that is adjacent to the peak of the second circumferential element being connected to a first connection element, and on the other side, to a peak of the third circumferential element that is longitudinally aligned with the peak of the second circumferential element.

In one embodiment of the scaffold, the peaks and valleys of the first circumferential element are substantially in-phase with the peaks and valleys of the second circumferential element, and each of the first connection elements connects a peak of the first circumferential element with a valley of the second circumferential element, the valley being adjacent to a peak of the second circumferential element that is longitudinally aligned with the peak of the first circumferential element. In a further embodiment, the peaks and valleys of the second circumferential element are substantially in-phase with the peaks and valleys of the third circumferential element, and each of the second connection elements connects, on one side, to a peak of the second circumferential element adjacent to the valley of the second circumferential element that is connected to the first circumferential element by a first connection element, and on the other side, to a valley of the third circumferential element which is adjacent to a peak of the third circumferential element that is longitudinally aligned with the peak of the second circumferential element, and each of the first connection elements is not longitudinally aligned with any of the second connection elements.

In one embodiment of the scaffold, when the scaffold is expanded, the scaffold comprises at least one contiguous spiral pattern that includes at least one of the first connection elements and at least one of the second connection elements, the at least one of the first connection elements and the at least one of the second connection elements both connect the second circumferential element at a same peak or valley. In an alternative embodiment of the scaffold, when the scaffold is expanded, the scaffold comprises at least one contiguous spiral pattern that includes at least one of the first connection elements and at least one of the second connection elements, where the at least one of the first connection elements connects the second circumferential element at a first connection location, the at least one of the second connection elements connects the second circumferential element at a second connection location different from the first connection location, the contiguous spiral pattern further comprising a portion of the second circumferential element between the first connection location and the second connection location.

In one embodiment, at least one of the circumferential elements includes a notch at a location where a connection element and the circumferential element intersect.

BRIEF DESCRIPTION OF THE DRAWINGS

FIG. 2A shows a cut pattern of the scaffold with the circumferential elements having varying lengths.

FIG. 2B shows the varying amplitude of circumferential elements.

FIG. 2C shows a repeating sinusoid pattern.

FIG. 4B-4F illustrates various embodiments of the various connection elements.

FIG. 4G shows a perspective view of a marker dot.

FIGS. 4H, 4J and 4K shows cross sections of various embodiments of marker dots.

FIG. 14C shows various embodiments of how the connection elements can be attached to adjacent circumferential elements.

FIGS. 15A-E illustrates where the connection elements can attach along the undulations.

FIG. 16 shows the radial displacement of the attachment of connection element to adjacent undulations.

FIGS. 17A1, 17A2 and 17B show an example of phasing in adjacent circumferential elements.

DETAILED DESCRIPTION OF THE INVENTION

Figure 1:
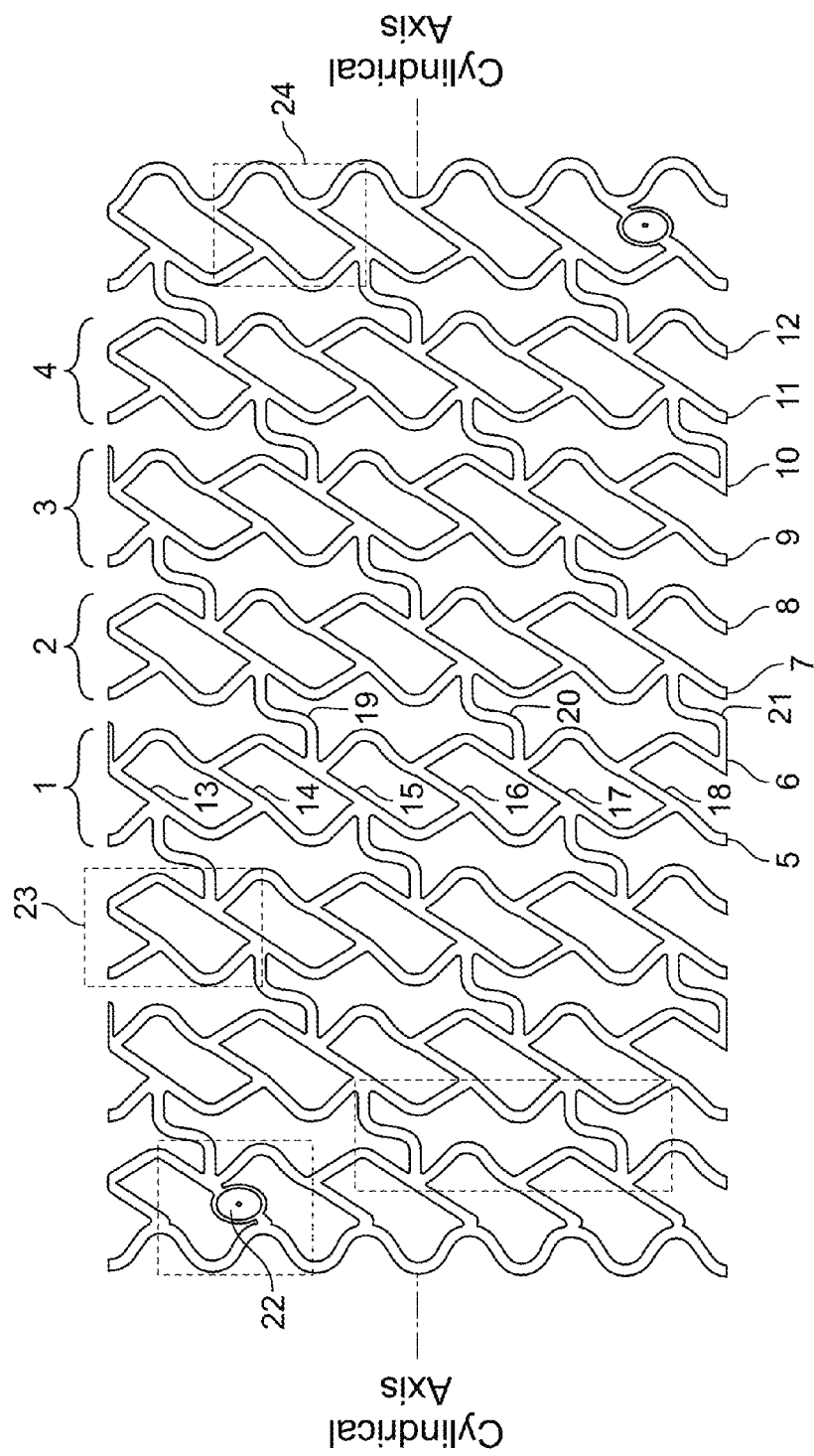
FIG. 1 shows a cut pattern of the scaffold.

The present invention relates to expandable vascular scaffolds including stents. The overall design of the scaffold is based on a modular design that comprises pairs of circumferential elements connected by one or more connection elements (the terms connecting and connection are used interchangeably here). Using a modular approach, the scaffold can be assembled from circumferential elements and connection elements that vary in length and design. When expanded, the connection elements form a spiral pattern, which can be a helix.

The vascular scaffolds may be formed from a bioabsorbable polymer, a biocorrodable or bioabsorbable metal, or combinations thereof. Non-limiting examples of bioabsorbable polymers include poly-L-lactide (PLLA), poly-D-lactide (PDLA), poly(D,L-lactide) (PDLLA), poly(desaminotyrosil-tyrosine ethyl ester) carbonate, poly(caprolactone) (PCL), and poly(anhydride ester) salicylic acid. Non-limiting examples of biocorrodable/bioabsorbable metal include iron, iron-based alloys, magnesium, magnesium-based alloys with or without rare earth elements, such as Mg—Sr alloys, Mg—Sr—Zn alloys, Mg—Zn—Zr alloys, Mg—Nd—Zn—Zr alloys, Mg—Zn—Al alloys. Mg—Zn—Ca alloys, and metallic glasses such as zirconium based metallic glasses.

The scaffolds may also be formed from various combinations of metals and polymers. U.S. Pat. Nos. 7,846,361; 7,897,224 and 8,137,603. U.S. Patent Publication No. 2010/0093946. Alexy, et al., BioMed Research International, 2013, Article ID 137985.

Generally, the scaffold is a cylindrical or tubular object having a cylindrical (or longitudinal) axis running the length of the cylinder. The modular geometric design of the present invention exhibits a high degree of flexibility and significant radial strength. Generally, the scaffolds have a primarily cylindrical shaped main body that has a plurality of expandable circumferential elements. The circumferential elements can vary in length. At least two circumferential elements may be connected to form a pair of circumferential elements. There may be one or more connection elements between the circumferential elements forming the pair of circumferential elements. The connection elements may be found in a variety of different geometric shapes, including linear, curvilinear or combinations of the two shapes. Each pair of circumferential elements is connected to an adjacent pair of circumferential elements by at least one connection element. The number of connection elements between circumferential elements in a pair or between pairs of circumferential elements can vary.

As used herein, the term "circumferential elements" refers to structural elements circumscribing the circumference of the present scaffold which may be in the form of a cylinder. In one embodiment, the circumferential element is bounded by two hypothetical planes which are substantially perpendicular to the cylindrical axis of the scaffold. A circumferential element may comprise (or consist of) a plurality of undulations. An undulation is a repeat unit within the circumferential element and can comprise a peak and a valley. The number of undulations per circumferential element can vary from 2-N, e.g., 2, 3, 4, 5, 6, 3, 4, 5, 6, 7, 8, 9, 10, 11, 12, 13, 14, 15, 16, 17, 18, 19, 20, 30, 40, 50, 60, etc.

When the vascular scaffold is expanded, at least a portion of the connection elements connecting the circumferential elements in the pairs and/or the connection elements connecting the circumferential elements in adjacent pairs form a contiguous spiral pattern.

In one embodiment, the contiguous spiral pattern is oriented substantially parallel to the cylindrical axis of the scaffold. The contiguous spiral pattern may also take other orientations. The contiguous spiral pattern may form a helix and there may be one or more helices in a particular embodiment, e.g., double or triple helix, or 4, 5, 6 or higher numbers of helices. When there is more than one helix, adjacent helices may be substantially parallel to each other.

Adjacent helices may not be parallel to each other. In one embodiment, there are two or more helices equidistant from the cylindrical axis of the scaffold.

The circumferential elements may be uniform in shape. Alternatively a circumferential element may be comprised of a variety of different shapes. For example, the circumferential elements may be formed from a series of undulations which may be in a sinusoidal pattern, a sawtooth pattern, a square wave pattern or any other type of repeating or non-repeating pattern, e.g., a combination of sinusoidal and sawtooth. The amplitude of the undulations may vary within one circumferential element or between two circumferential elements (amplitude is the peak deviation of the function from zero). The amplitude and frequency of the undulations can also vary. For example, a circumferential element can be comprised of a sinusoidal pattern having a repeated pattern of varying amplitudes, 2:1:2:1, 2:1, etc., where, the ratio of the amplitudes of the undulations are represented by the ratio shown. Other ratios are also possible, 3:1, 4:1, 5:1, etc. The circumferential elements may be comprised of one or more segments with each segment having its own undulation pattern. The number of segments in each circumferential element may vary from 1 to N, e.g., 1, 2, 3, 4, 5, 6, 7, 8, 9, 10, 11, 12, 13, 14, 15, 16, 17, 18, 19, 20, 30, 40, 50, 60, etc. The shape of the segments may be linear or curvilinear. Thus, the circumferential element can be assembled in a modular fashion from various segments which may be alike or different. In the scaffold, the length of all the circumferential elements may be the same. Alternatively, the length of the circumferential elements may vary, e.g., in several different ways. For example, the length of the circumferential elements within one pair may be the same, while the length of the circumferential elements closer to one end of the scaffold may be greater than or less than the length of the circumferential elements closer to the middle of the scaffold.

The number of connection elements connecting adjacent circumferential elements (first connection element, or second connection element) can range from 1 to N, e.g., 1, 2, 3, 4, 5, 6, 7, 8, 9, 10 or higher numbers, 10-20. The shape of the connecting elements may be linear, curvilinear, S-shaped, reverse S-shaped, Z-shaped, reverse Z-shaped, or any other combination of shapes, including, for example, a linear and curvilinear section. Similarly, the number of connecting elements connecting adjacent pairs of circumferential elements may range from 1 to N (e.g., 1, 2, 3, 4, 5, 6, 7, 8, 9 or 10) and the shape of such connecting elements may be linear, curvilinear, S-shaped, reverse S-shaped, Z-shaped, reverse Z-shaped, or any combination thereof. The connecting elements may assume a variety of angles relative to the cylindrical axis of the scaffold, including, 0-20°, 20-40°, 40-60° or 60-80°; furthermore, the angle of these connecting elements may be positive or negative relative to the cylindrical axis of the scaffold. If the connecting elements are curvilinear, they may be concave and convex with the curvature present at selected portions of the connecting elements; the degree of curvature may also vary within one connecting element. The number of connecting elements can be adapted to modify the flexibility of the scaffold with decreasing flexibility generally being present as the number of connecting elements increases.

When the connection element is S-shaped, it may have a substantially S-shaped structure. In one embodiment, the S-shaped connection elements have a double curved structure which allows for more slack between circumferential elements, enabling greater expansion of the scaffold. The longer this S-shaped segment, the more slack and expandability there is in the structure. An S-shaped connection element may be smooth or may be angular. In another embodiment, the S-shaped connection element includes at least three substantially linear portions: a first linear portion being substantially parallel to the cylindrical axis of the scaffold (e.g., forming an angle between about 0 degree and about 20 degrees with respect to the cylindrical axis of the scaffold); a second linear portion being substantially perpendicular to the axis (e.g., forming an angle between about 70 degree and about 90 degrees with respect to the cylindrical axis of the scaffold); and a third linear portion being substantially parallel to the axis (e.g., forming an angle between about 0 degree and about 20 degrees with respect to the cylindrical axis of the scaffold). In still another embodiment, the S-shaped connection element includes at least three substantially linear portions: a first linear portion being substantially parallel to the cylindrical axis of the scaffold (e.g., forming an angle between about 0 degree and about 20 degrees with respect to the cylindrical axis of the scaffold); a second linear portion being substantially perpendicular to the first linear portion (e.g., the second linear portion forming an angle between about 70 degree and about 90 degrees with respect to the first linear portion); and a third linear portion being substantially parallel to the first linear portion (e.g., the third linear portion forming an angle between about 0 degree and about 20 degrees with respect to the first linear portion) or perpendicular to the second linear portion (e.g., the third linear portion forming an angle between about 70 degree and about 90 degrees with respect to the second linear portion).

When the connection element is Z-shaped, it has a substantially Z-shaped structure.

When there is more than one connection element between adjacent circumferential elements, the connection elements are positioned symmetrically or asymmetrically at radial positions along the circumference of the scaffold. If the connection elements are positioned symmetrically, the radial distance between each pair of connection elements, e.g., A-B and B-C, is equal.

The radial positions listed for the connection elements here are only provided for illustration purposes and the connection elements may be positioned by one of ordinary skill in the art without undue experimentation at any point along the circumference of the scaffold with respect to the cylindrical axis. For example, the positioning of the connection elements may be determined by dividing 360° by n where n is the number of connection elements between adjacent circumferential elements. Where n=3, the connection elements may be positioned symmetrically at approximately 120° intervals around the circumference of the stent. When there are two equally spaced connection elements between adjacent circumferential elements, they are situated approximately 180° with respect to one another. In other words, the two connection elements are oppositely oriented with respect to one another.

For the purposes of reference only, the connection elements connecting the circumferential elements in each pair are referred to as first connection elements, while connection elements connecting the circumferential elements in adjacent pairs of circumferential elements are referred to as second connection elements. The first and second connection elements may be of the same shape or have different shapes. In addition, the shape of the first connection elements connecting the circumferential elements in a pair of circumferential elements may be the same or may very in both shape and length. Similarly, the connection elements connecting adjacent pairs of circumferential elements may be the same or may vary in shape and length. As discussed further below, the first and second connection elements may be configured to allow the vascular scaffold to expand without causing the circumferential elements forming the pairs to significantly bend out of the plane formed by the circumferential element after expansion. Thus, the connection elements between adjacent pairs of circumferential elements (e.g., the second connection elements) may be able to elongate in response to expansion of the scaffold. In one embodiment, these connection elements have an S-shape or are curvilinear.

When the scaffold is expanded, at least a portion of the connection elements connecting the circumferential elements in the pairs and/or the connection elements connecting the circumferential elements in adjacent pairs form a contiguous spiral or helical pattern. In one embodiment, the spiral or helical pattern comprises at least a portion of the first and second connection elements. In another embodiment, the spiral pattern comprises at least a portion of the first connection elements. In a third embodiment, the spiral pattern comprises at least a portion of the second connection elements. In a fourth embodiment, the spiral pattern comprises at least a portion of the first and second connection elements, and at least a portion of the circumferential elements. In a fifth embodiment, the spiral pattern comprises at least a portion of the first connection elements, and at least a portion of the circumferential elements. In a sixth embodiment, the spiral pattern comprises at least a portion of the second connection elements, and at least a portion of the circumferential elements.

The length of a connection element refers to the absolute distance of travel along the connection element starting from one end of the connection element traveling along the distance to the other end of the connection element.

The length of the second connection element can be greater than, equal to or less than the length of the first connection element.

The undulations of the circumferential elements can form peaks and valleys with respect to either proximal or distal end of the vascular scaffold. The first connection elements can connect the circumferential elements in the pair from peak to peak, peak to valley, or valley to valley. Similarly, the second connection elements can connect the circumferential elements between adjacent pairs from peak to peak, peak to valley, or valley to valley. The peak to peak, peak to valley, or valley to valley connections may be between circumferential elements that are in the same cylindrical axial line or shifted by 180° degrees; other shifts, include, but are not limited to, 5°, 60°, 90° and 120° degrees from the same cylindrical axial line. The connection elements may connect any points on adjacent circumferential elements, including, but not limited to, peak, valley, any point on the ascending portion or descending portion of an undulation.

The undulations of one circumferential element in a pair may either be in phase or out of phase with the undulations of the other circumferential element in the pair. If the two circumferential elements are out of phase, the degree of phase difference may range from greater than 0° to 180° degrees, including, but not limited to, 5°, 60°, 90° and 120° degrees.

Similarly, the undulations of one pair may either be in phase or alternatively out of phase with the undulations of an adjacent pair. If the two circumferential elements are out of phase the degree of phase difference may range from greater than 0° to 180° degrees, including, but not limited to, 5°, 60°, 90° and 120° degrees.

The undulations of adjacent circumferential elements may either be in phase or out of phase. If the two circumferential elements are out of phase, the degree of phase difference may range from greater than 0° to 180° degrees, including, but not limited to, 5°, 60°, 90°, 120 and 180° degrees.

When a radial expanding force is applied to the scaffold, such as through an expandable balloon, the circumferential elements expand radially and elongate circumferentially. Conversely, when an external compressive force is exerted on the scaffold, the circumferential elements contract radially and shorten circumferentially. When a radial expanding force is applied to the scaffold, the undulations decrease in amplitude. Conversely, when an external compressive force is exerted on the scaffold, the undulation increases in amplitude.

In another embodiment, the scaffold comprises a plurality of polygons. The polygon has n-sides where n is any positive integers. For example, the polygons may have sides ranging from 3 to 30 (higher order polygons are also encompassed by the designs of the present invention), e.g., 3, 4, 5, 6, 7, 8, 9, 10, 11, 12, 13, 14, 15, 16, 17, 18, 19, 20, 21, 22, 23, 24, 25, 26, 27, 28, 29 and 30 sided polygons, up to an n-sided polygon. The sides of the polygons may be equal or unequal. The opposite sides in a polygon may be substantially parallel to each other when the scaffold is crimped. Opposite sides in a polygon may also take other configurations in relation to each other.

The polygon may be formed from a plurality of undulations which are connected by a plurality of connection elements. For example, the polygon may be a hexagon formed from two undulations connected by two connection elements; a hexagon may comprise a first undulation and a second undulation, which are connected by a first segment and a second segment. The filaments comprising the first and second undulations in each hexagon may have different or identical width, length and thickness. The polygon may also be formed from a plurality of undulations without connection elements. For example, the polygons may be tetragons consisting of two undulations. In higher-order polygons, e.g., n=8–30, the undulations may be connected by a plurality of connection elements.

An undulation may comprise one segment or at least two segments (e.g., 3, 4, 5, 6, 7, 8, 9, 10, 11, 12, 13, 14, 15, 16, 17, 18, 19, 20, 30, 40, 50, 60, N segments). The segments may be linear or curvilinear. When a segment is curvilinear, the degree of curvature may vary. A segment may be concave or convex. A segment may contain solely linear portions joined together, or solely curved portions joined together. Alternatively, a segment may contain both linear portions and curved portions that are joined together. The segment may comprise at least one bend placed at selected points along its length. For example, a segment may take the shape of a stylized n, C, U, V, etc. A segment may also be in the shape of a loop where the loop may be circular or semicircular. The segment can essentially assume any suitable configuration. The length, width and thickness of the segments of the undulations may be equal or unequal. The two undulations of each polygon across each circumferential component may be identical or may vary. A wide variety of different configurations for the polygons as well as the various segments representing the sides of the polygon are encompassed by the present invention. For example, the segments representing the sides of the polygon may be linear or curvilinear. In one polygon, the length of the segments comprising one undulation may be equal to or greater than the length of the segments of the opposing undulation. The polygon may be convex (i.e., all its interior angles are less than 180°) or non-convex (i.e., it contains at least one interior angle greater than) 180°. The polygons can form a continuous, interconnected structure across the body of the scaffold. A circumferential element (or a pair of circumferential elements) may contain different or substantially identical polygons. The polygons of different circumferential element may be different or substantially identical. The surface area of adjacent polygons may be equal or unequal. The surface area of the polygons, i.e., the area encompassed by the sides, can be calculated mathematically from the length of the sides of the polygon. http://mathworld.wolfram.com/PolygonArea.html, April, 2009.

One embodiment of the scaffold of the present invention is illustrated in FIG. 1. The pairs of circumferential elements are shown as 1-4. The circumferential elements in the scaffold for pairs 1-4 are labeled in parentheses, 1 (5, 6), 2 (7, 8), 3 (9, 10) and 4 (11, 12). The connection elements (first connection elements) between two circumferential elements in one pair, 1, are shown as 13-18, while the connection elements between adjacent pairs of circumferential elements 1 and 2 (second connection elements) are shown as 19-21. The scaffold may contain a marker dot, 22. Polygons formed by the undulations and the connection elements of the scaffold are illustrated by the boxes at 23 and 24.

Figure 2D:
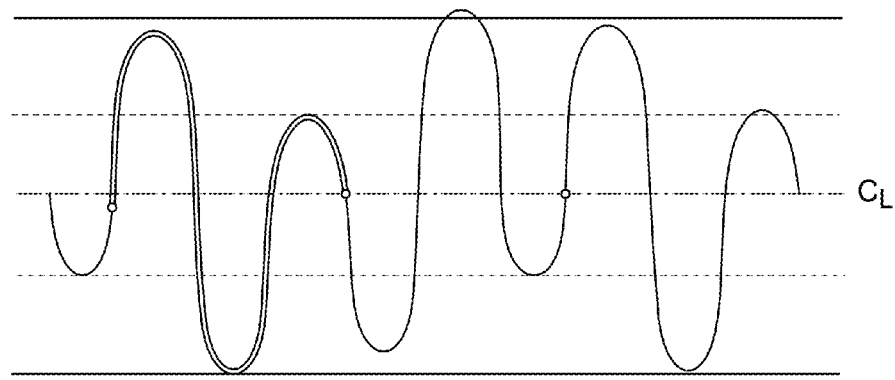
FIG. 2D shows a non-repeating sinusoid pattern.

Another embodiment of the scaffold is shown in FIG. 2A, here, the circumferential elements of the scaffold vary in length. The circumferential length of the circumferential elements are A>B>C; however, this order of lengths is shown only for illustration purposes. The amplitude of the undulations formed by the circumferential elements A, B, C, in a partially crimped or fully crimped state also has the length or height of A'>B'>C' (FIG. 2B). In the embodiment shown, the circumferential elements with varying lengths are distributed along the body of the scaffold as follows: A-B (25, 26), C-C (27, 28), C-C (29, 30), C-B (31, 32), B-B (33, 34), B-B (35, 36), and B-A (37, 38). However, numerous other combinations and distributions are possible as well. FIG. 2C shows a repeating sinusoidal pattern where the amplitude of the undulations is constant across the circumferential element. FIG. 2D shows a non-repeating sinusoid pattern. In a non-repeating sinusoid pattern, the amplitude and/or ordinary frequency of the undulations may vary either systematically or randomly along the circumference of the circumferential element.

The length of a circumferential element refers to the absolute distance of travel along the circumferential element starting from an artificial point on the circumferential element and back around to the same artificial point.

Figure 3:
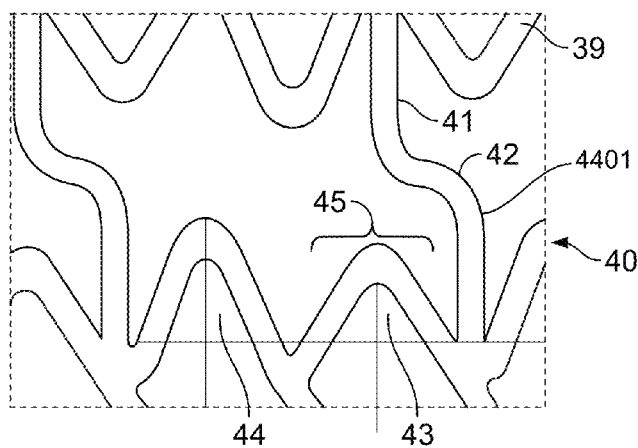
FIG. 3 shows a detailed view of adjacent circumferential elements.

A detailed view of one part of the undulations forming two adjacent pairs of circumferential elements is shown in FIG. 3. The circumferential elements are shown as 39, 40. They are connected by a connection element (second connection element), which has two linear portions, 41, 4101 and an S-shaped portion 42. The undulations of the circumferential element 40 have amplitudes 43 and 44. In the embodiment shown, 44 is greater than 43.

Figure 4A:
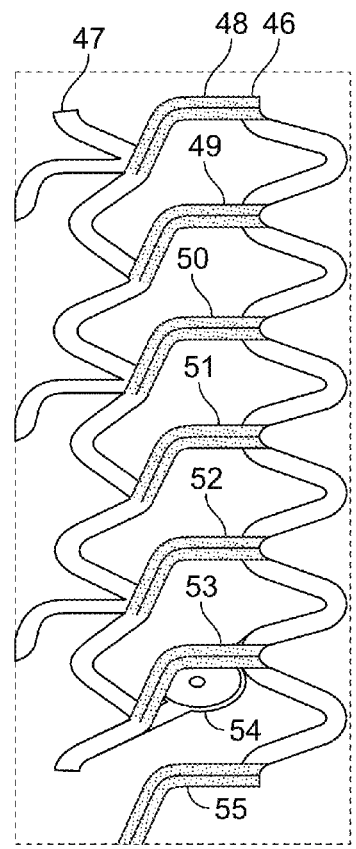
FIG. 4A shows the details of the connection elements at one end of the scaffold.

FIG. 4A shows the details of the connection elements (first connection elements) at one end of the scaffold. Circumferential elements 46, 47 are connected by connection elements (first connection elements) 48-55. FIGS. 4B-4F illustrates various embodiments of where the marker dot, 54, can be attached to the connection element, 56-59, at various points along the connection element 53, e.g., at a point along (and interrupting) or on the side of a linear, multi-segment or bent, or curvilinear connection element. FIG. 4G shows a perspective view of a marker dot 251. FIGS. 4H, 4J and 4K show cross sections of various embodiments of marker dot 252. The section of a scaffold for a marker dot can take various forms, including, but not limited to, a see-through void (FIG. 4H), a cup-shaped structure having a mouth 253, a bottom 254, and a hole 255 in the bottom (FIG. 4J), and a cup-shaped structure having a mouth 253a and bottom 254a (FIG. 4K).

Figure 5A:
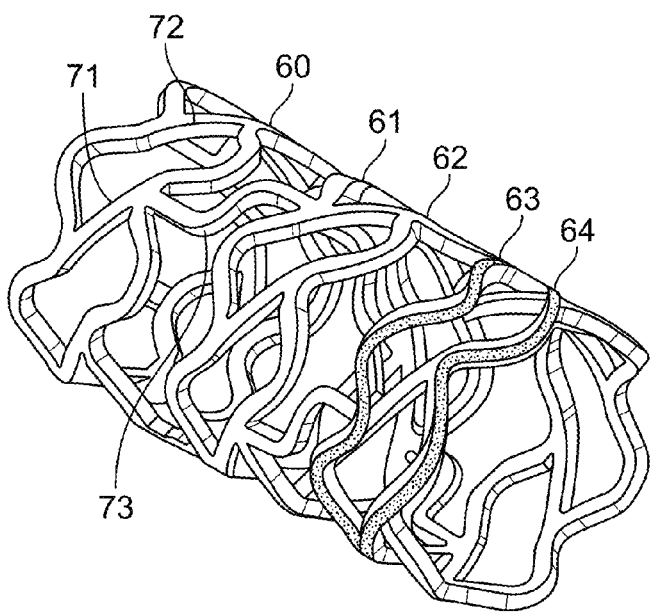
FIGS. 5A-5C show three dimensional views of the scaffold from various angles.
Figure 5B:
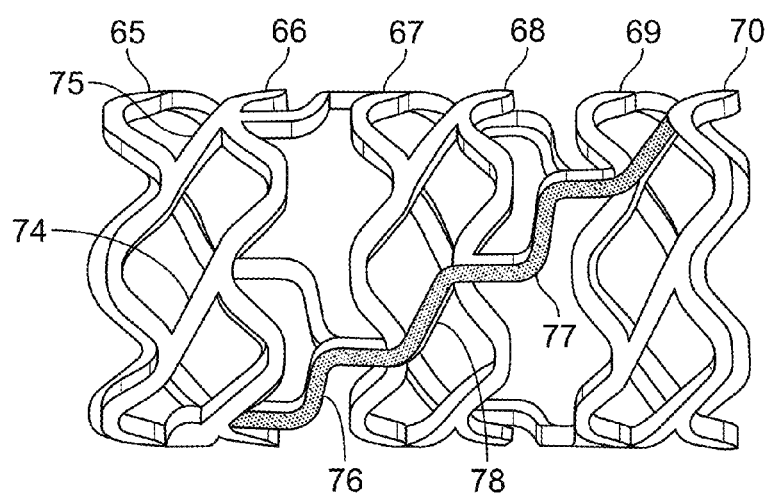
Figure 5C:
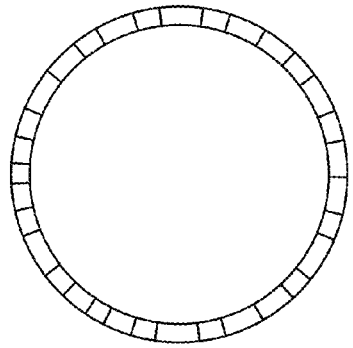

FIGS. 5A-5C show the scaffold in an orthogonal (5A), side (5B) and end (5C) views. The circumferential elements are labeled 60-64 and 65-70. The connection elements between pairs of circumferential elements are shown as 71, 72, 74, 75 (first connection element), while the connection element between two pairs is labeled 73. The formation of the spiral design is shown as 76-78 and contains the connection elements between pairs of circumferential elements as well as the connection elements between circumferential elements forming the pair (first and second connection elements, respectively). The circumferential elements forming a pair are shown with highlighted lines 63, 64.

Figure 6:
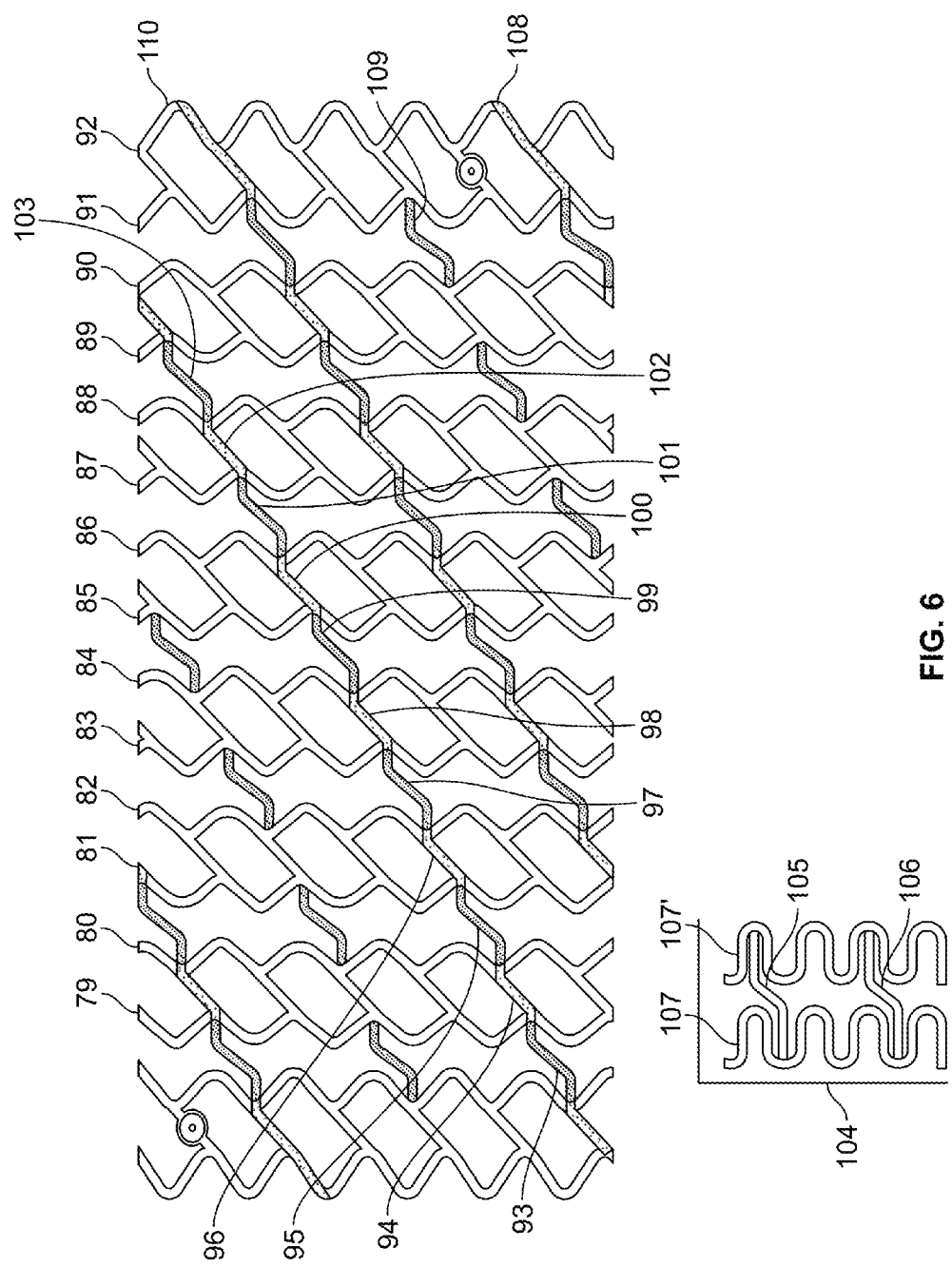
FIG. 6 shows a cut pattern of another embodiment of the scaffold.

FIG. 6 shows a cut pattern of another embodiment of the scaffold. The circumferential elements are labeled 79-92, with the pairs of circumferential elements being shown as 79,80; 81,82; 83,84; 85,86; 87, 88; 89,90 and 91, 92. The spiral pattern is shown as 93-103 and comprises an alternating pattern of connection elements between pairs of circumferential elements (second connection elements), 93, 95, 97, 99, 101 and 103, with connection elements between the circumferential elements forming a pair (first connection elements), 94, 96, 98, 100 and 102. In the inset to FIG. 6, a partially compressed view of the scaffold is shown. The circumferential elements are labeled 107, 107', while the connection elements are labeled 105, 106. The scaffold shown in the figure contains more than one spiral pattern, 108-110 which may be substantially parallel to one another.

Figure 7:
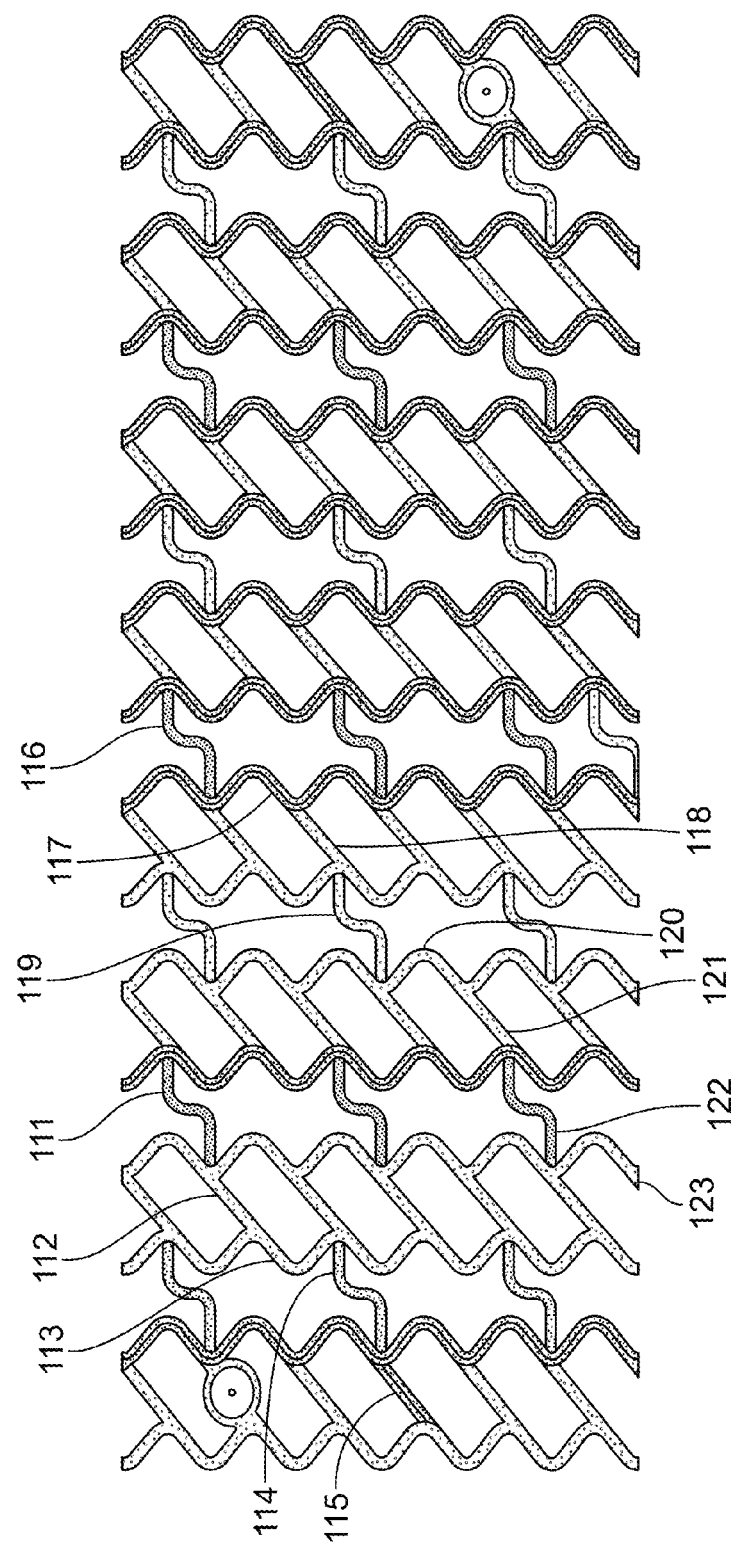
FIG. 7 shows a cut pattern of the scaffold with an alternative spiral pattern.
Figure 8:
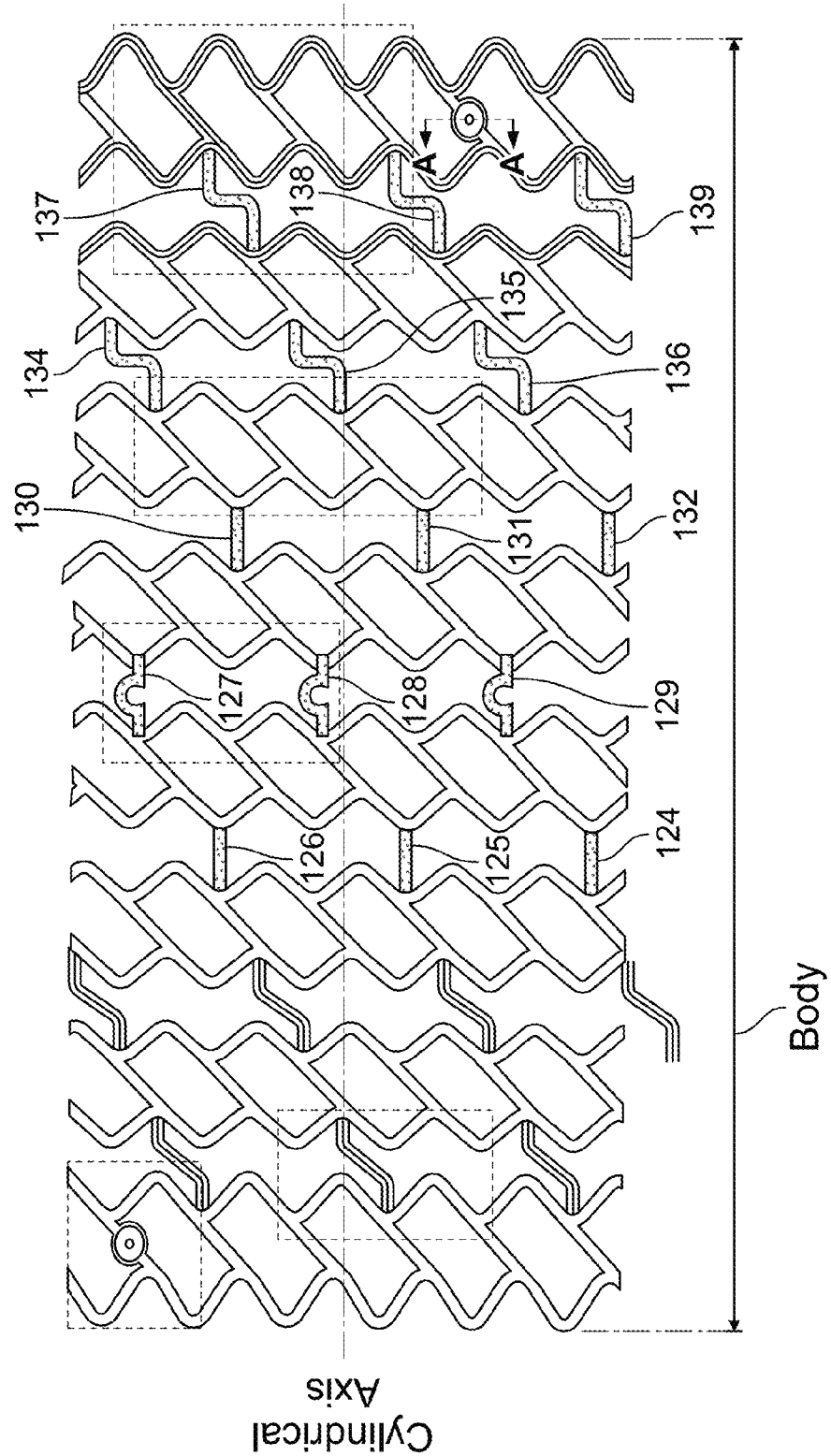
FIG. 8 illustrates a cut pattern of the scaffold containing a variety of connection elements with different shapes.

FIG. 7 shows a cut pattern of the scaffold with an alternative spiral pattern. In this embodiment, the spiral pattern is formed from an alternating pattern of connection elements between pairs of circumferential elements (first connection elements), 112, 115, 118, 121, portions of the undulations of the circumferential elements, 113, 117, 120, and connection elements connecting two adjacent pairs of circumferential elements (second connection elements), 111, 114, 116, 119, 122. In this embodiment, the spiral pattern has the following repeating sequence starting from one end of the scaffold: first connection element, second connection element, portion of the undulation, first connection element, second connection element, a portion of the undulation, which is repeated across the scaffold. Other repeating sequences are possible, including, but not limited to, (a) first connection element, portion of the undulation, first connection element, repeated n times across the body of the scaffold; (b) first connection element, portion of the undulation, repeated n times across the body of the scaffold; (c) second connection element, portion of the undulation, repeated n times across the body of the scaffold; or (d) second connection element, portion of the undulation, second connection element, repeated n times across the body of the scaffold;

FIG. 8 shows an embodiment where the connection elements have a variety of different shapes and the distribution of the pattern of the connection elements varies across the body of the scaffold. Specifically, in the embodiment shown, the connection elements between pairs of circumferential elements, are linear, 124-126 and 130-132 or curvilinear, 127-129, 134-136 and 137-139. One of the curvilinear connection elements between pairs of circumferential elements have both linear and curvilinear portions, 127-129. As is evident from the illustration, the pattern of connection elements can vary across the body of the scaffold, curvilinear, 137-139, 134-136, linear, 130-132, curvilinear, 127-129 and linear, 124-126. Other possible arrangements as well as geometric shapes are encompassed by the invention. One of ordinary skill in the art can select the sequence and type of connection elements to fit the flexibility and spatial requirements posed by the vasculature.

Figure 9:
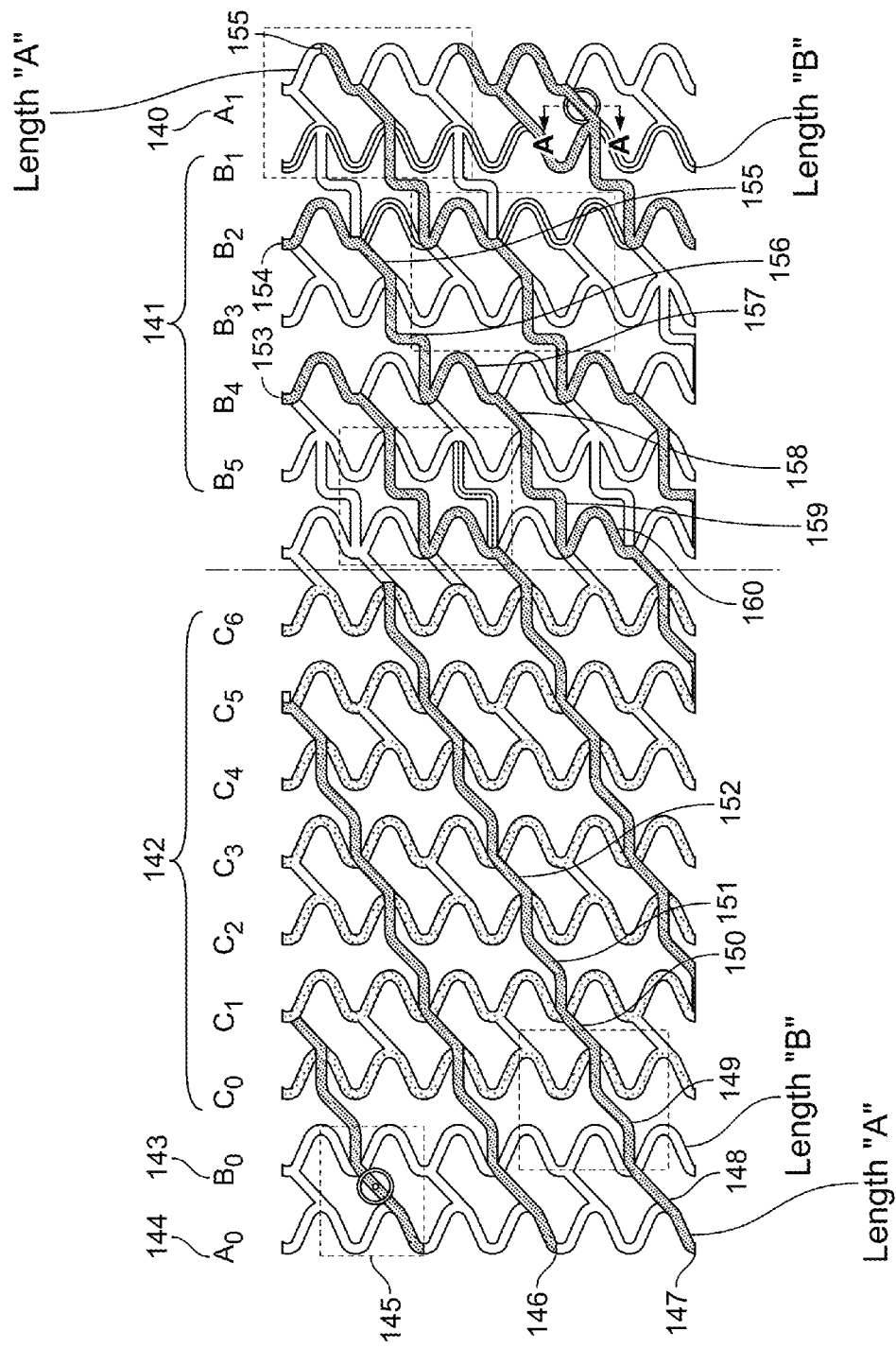
FIG. 9 shows a cut pattern of the scaffold with an alternative spiral pattern together with circumferential elements of varying length.

FIG. 9 shows a cut pattern of the scaffold with an alternative spiral pattern together with circumferential elements of varying length. This embodiment illustrates the modular design nature of the scaffold where circumferential elements of differing lengths as well as a variety of different connection elements are combined to form a scaffold having two different spiral patterns. The circumferential elements have lengths, $A_n$, $B_n$ and $C_n$. For example, in one embodiment, the circumferential lengths are A>B>C. Specifically, A1 and A0 (140, 144) are combined with $B_0$-$B_5$ (141, 143) which in turn are combined with $C_0$-$C_6$ (142) in the sequence shown in FIG. 9. There are two different spiral patterns present in this embodiment, 145-147, and 153-154. The spiral pattern in 147 comprises a connection element between the circumferential elements forming the pair (first connection elements), 148, 150, 152 and the connection element between pairs of circumferential elements (second connection elements), 149, 151. The other spiral pattern, 154, comprises a connection element between the circumferential elements forming the pair (first connection elements), 155, 158, a portion of the undulation of the circumferential element, 157, 160 and the connection element between pairs of circumferential elements (second connection elements), 156, 159.

Figure 10A:
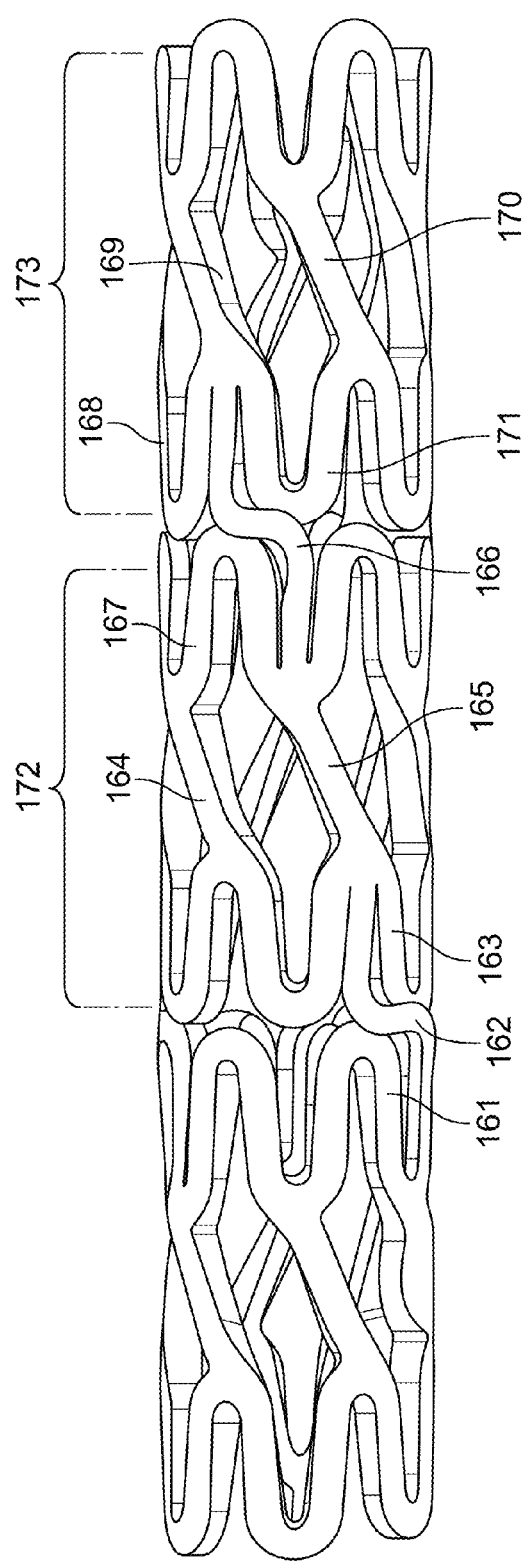
FIGS. 10A and 10B show side views of a three-dimensional perspective of the scaffold in a crimped state.
Figure 10B:
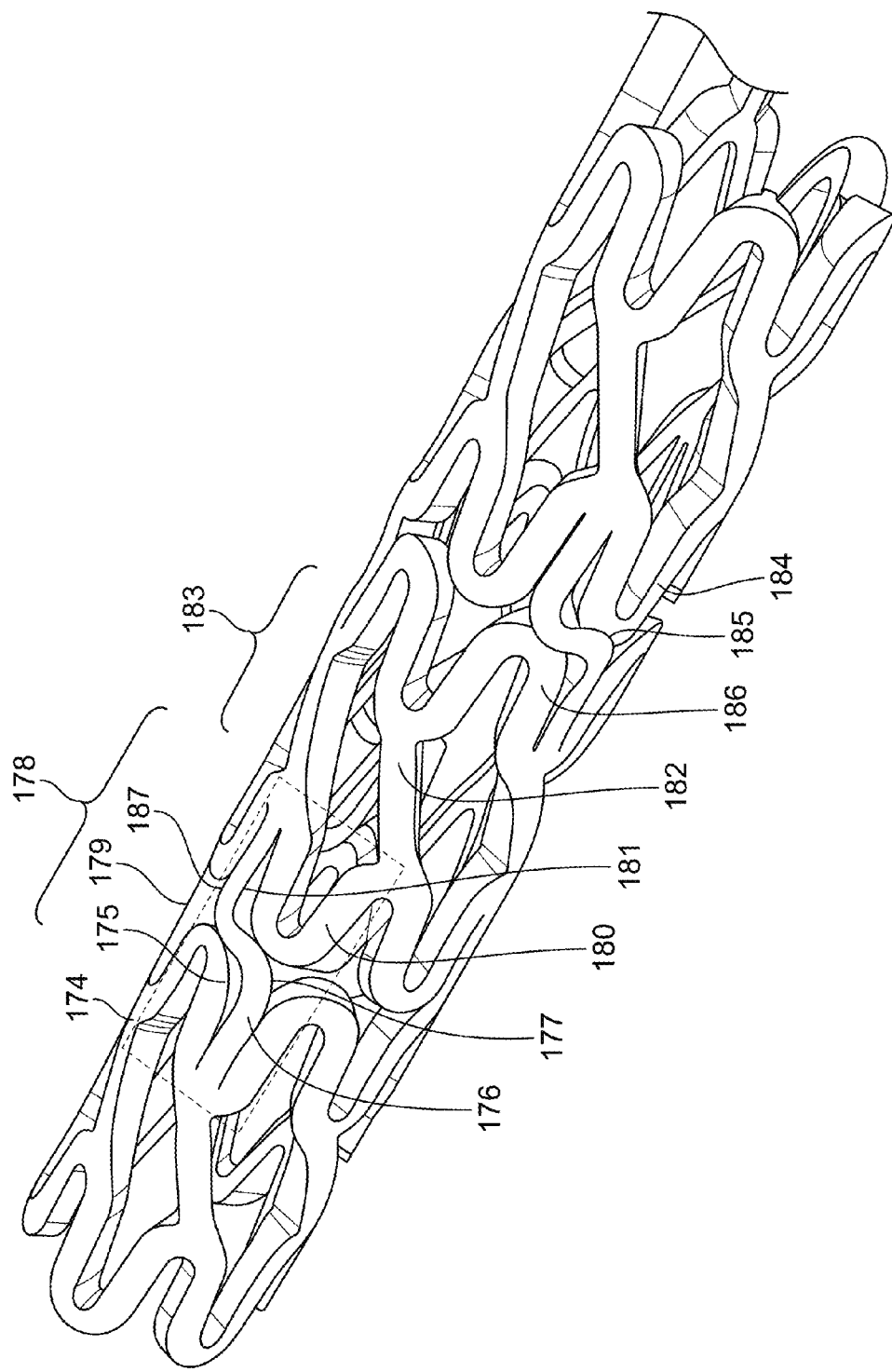

FIGS. 10A and 10B show side views of a three-dimensional perspective of the scaffold in a crimped or compressed state. The pairs of circumferential elements are shown as 172,173. One undulation forming part of a circumferential element 161,167 is adjacent to a connection element between the pairs of circumferential elements 162, 166 (the second connection element). This connection element sits on top or nestles/nests, but does not necessarily touch, the undulation of a circumferential element in an adjacent pair 163, 171. The connection elements connecting the circumferential elements in a pair are shown as 169, 170 (the first connection element). This arrangement can also be seen clearly in FIG. 10B where one undulation forming part of a circumferential element 175,186 is adjacent to a connection element between the pairs of circumferential elements 176, 185 (the second connection element). This connection element sits on top or nestles/nests the undulation of a circumferential element in an adjacent pair 180, 184. The connection elements connecting the circumferential elements in a pair are shown as 182 (the first connection element). A pair of circumferential elements is labeled as 183.

Figure 11B:
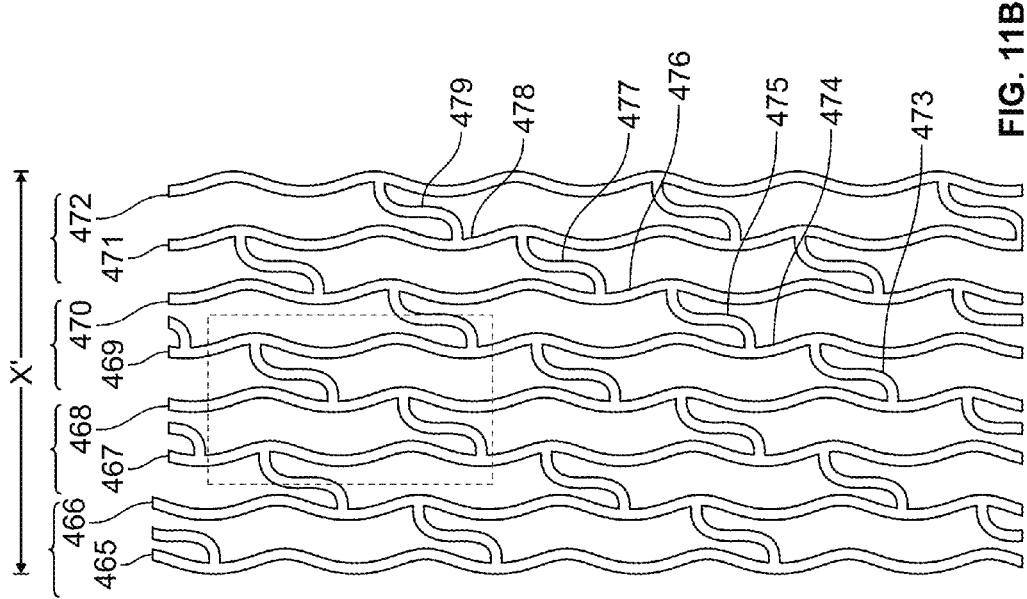
FIGS. 11A and 11B illustrate cut patterns of the present scaffolds with alternative spiral patterns.
Figure 11A:
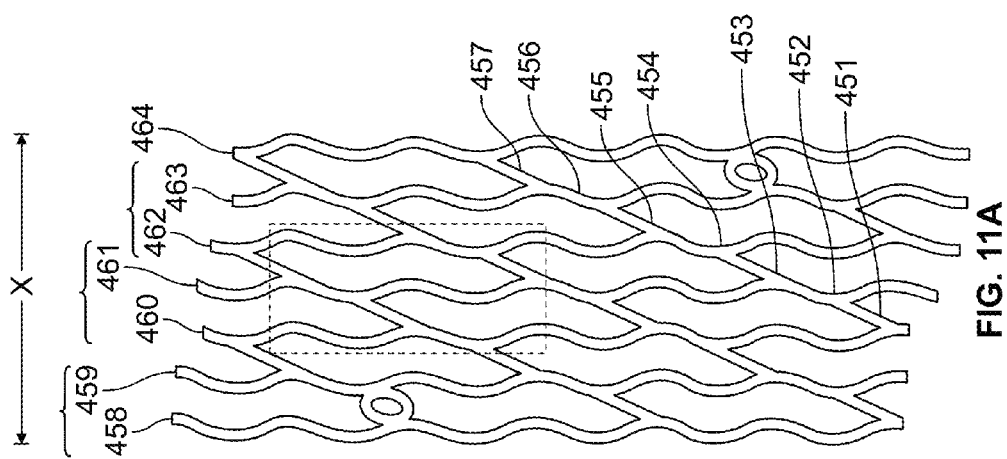

FIG. 11A shows a cut pattern of the scaffold with an alternative spiral pattern. The circumferential elements are labeled 458-464, with the pairs of circumferential elements being shown as 458, 459; 460, 461 and 462, 463. In this embodiment, the spiral pattern is formed from an alternating pattern of connection elements between pairs of circumferential elements (first connection elements), 451, 455, portions of the undulations of the circumferential elements, 452, 454, 456, and connection elements connecting two adjacent pairs of circumferential elements (second connection elements), 453, 457. In this embodiment, the spiral pattern has the following repeating sequence starting from one end of the scaffold: first connection element, portion of the undulation, second connection element, portion of the undulation, which is repeated across the scaffold. In FIG. 11A, both the first and second connection elements are linear.

FIG. 11B shows a cut pattern of the scaffold with another spiral pattern. The circumferential elements are labeled 465-472, with the pairs of circumferential elements being shown as 465, 466; 467, 468; 469, 470 and 471, 472. In this embodiment, the spiral pattern is formed from an alternating pattern of connection elements connecting two adjacent pairs of circumferential elements (second connection elements), 473, 477, portions of the undulations of the circumferential elements, 474, 476, 478, and connection elements between pairs of circumferential elements (first connection elements), 475, 479. In this embodiment, the spiral pattern has the following repeating sequence starting from one end of the scaffold: second connection element, portion of the undulation, first connection element, portion of the undulation, which is repeated across the scaffold. In FIG. 11B, both the first and second connection elements are S-shaped.

One of the issues with the prior art designs is that, when the scaffold expands, the undulations forming adjacent circumferential elements are distorted. The present design is an improvement.

Figure 12:
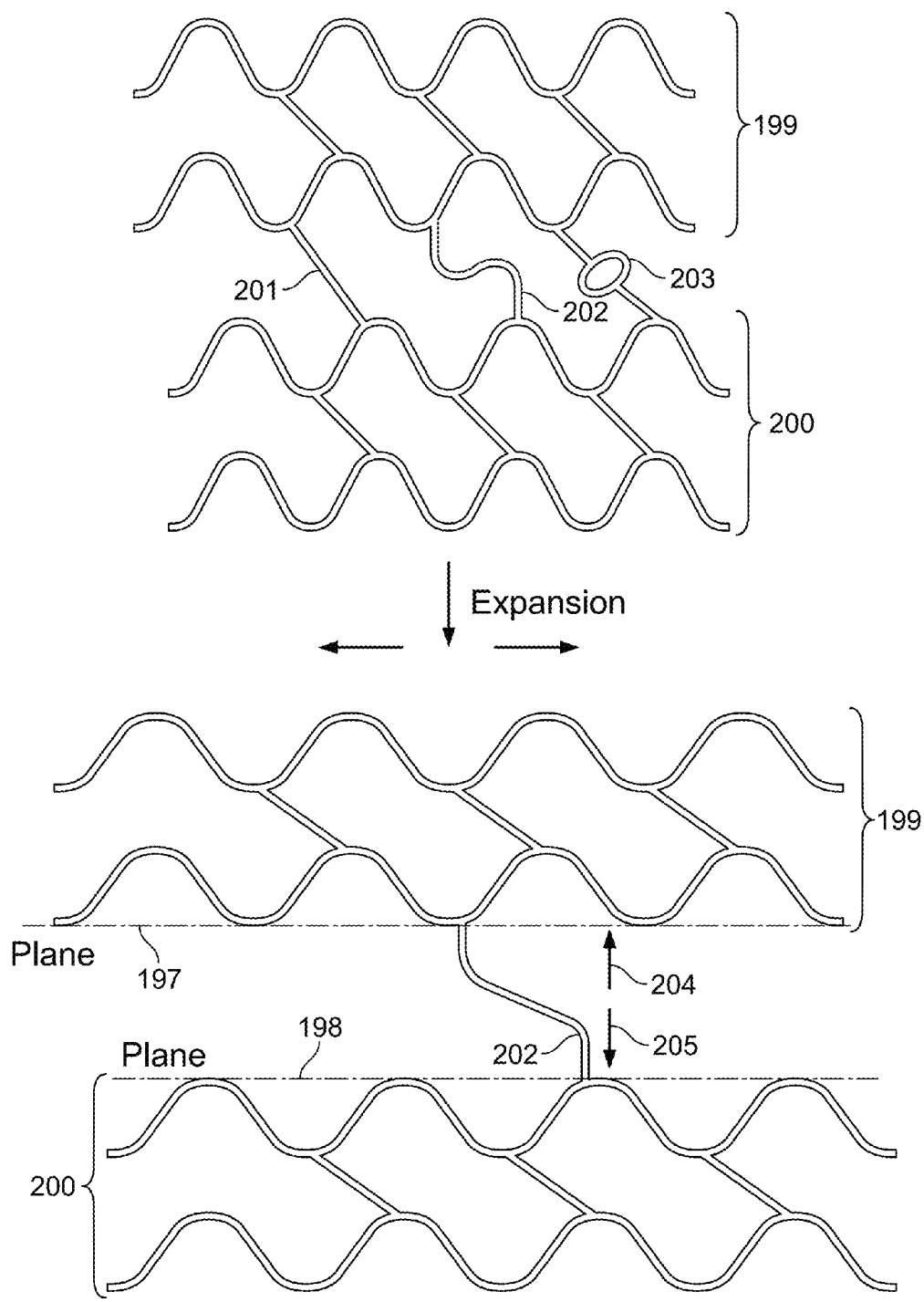
FIG. 12 illustrates the functionality of the connection element.

FIG. 12 illustrates the functionality of the connection element between adjacent pairs of circumferential elements. 199 and 200 are pairs of circumferential elements. Three types of connection elements are illustrated, linear, 201 and curvilinear 202, 203. When the scaffold expands, connection element 201 is restrictive and cannot accommodate expansion of the circumferential elements; however, either connection element 203 or 203 are less restrictive and accommodate expansion without distorting the circumferential elements in adjacent pairs out of the plane, 197, 198.

Figure 13:
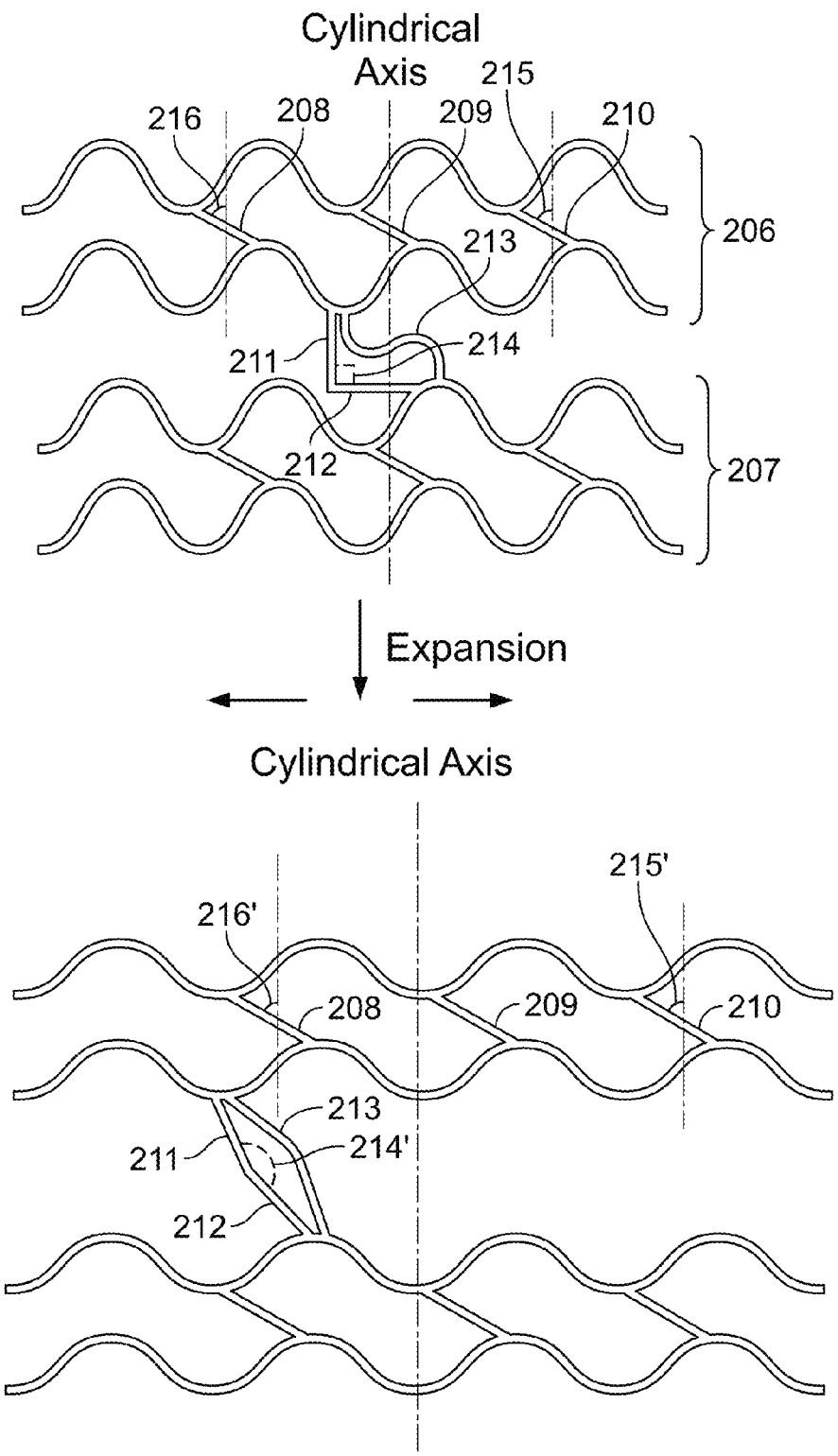
FIG. 13 illustrates the geometry of the scaffold and connection elements (first and second connection elements) on expansion.

FIG. 13 illustrates the geometry of the scaffold and the connection elements on expansion. The pairs of circumferential elements are shown as 206, 207. The connection elements between the undulations (first connection element) forming the pairs of circumferential elements are labeled 208-210. The connection element between pairs is labeled 213. The geometry of expansion is illustrated by creating a triangle with 213 using 211,212. The angle formed with respect to the cylindrical axis for 208 and 210 is labeled 215, 216. The angle formed with 211, 212 and 213 is labeled 214. After expansion, the angles 214', 215' and 216' all increase.

Figure 14A:
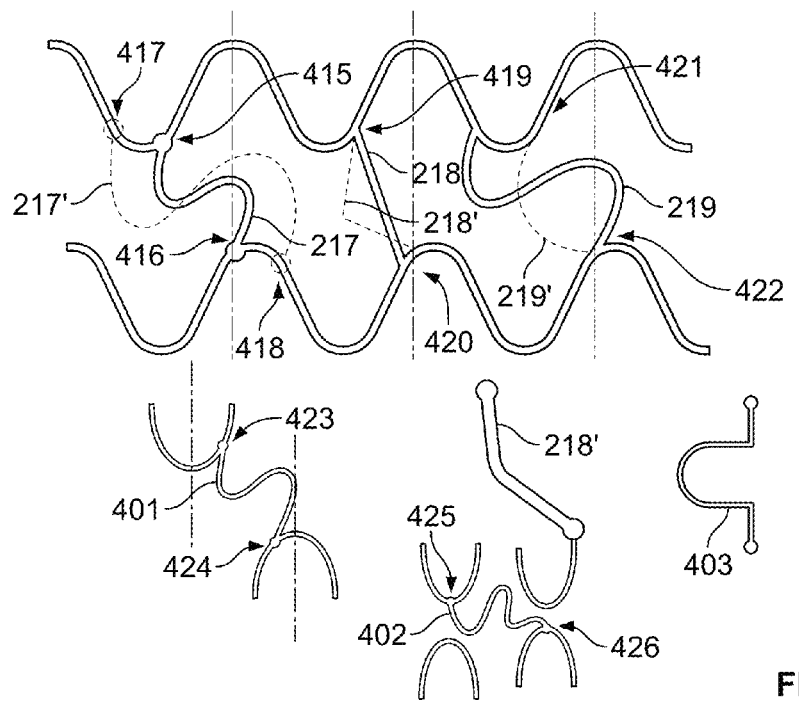
FIGS. 14A and 14B illustrate the geometry of the connection elements.
Figure 14B:
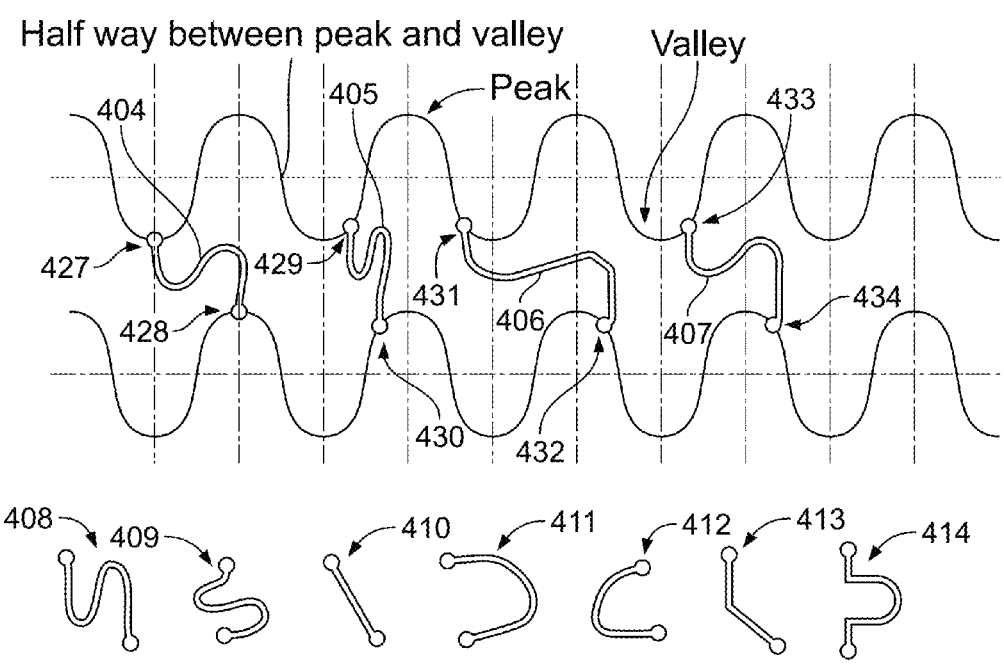

FIGS. 14A and 14B illustrate various embodiments of the structural geometry of connection elements which may be between circumferential elements in a pair (first connection elements) or between adjacent pairs of circumferential elements (second connection elements). The connection elements can be S-shaped, 217, 217', 401, 404-409, linear, 218, 410, 218', 413 (bent), concave/convex 219, 219', 411, 412, curvilinear, 402, 403, 414. The connection elements may connect any points on adjacent circumferential elements, including, peak (426, 428,), valley (425, 427,), or any point on the ascending portion (415, 416, 419, 420, 421, 422, 423, 424, 429, 430, 433) or descending portion (417, 418, 431, 432, 434) of an undulation.

FIG. 14C shows that, with one end of the connection elements being attached to a point on an undulation of a circumferential element, the other end of the connection element may be attached to the direct corresponding peak or valley of the adjacent circumferential element, or to a point shifted by 1, 2, 3, 4, 5, 6, 7, 8, 9 . . . N (N can be any positive integers) undulations (the shift may be towards either directions). In FIG. 14C, the two ends of the connection elements are: 480 (peak), 481 (valley); 482 (peak), 483 (valley shifted by 1 undulation); 484 (peak), 485 (valley shifted by 1 undulation); 486 (valley), 487 (peak).

FIGS. 15A-E illustrates where the connection elements can attach along the undulations. The connection elements here are shown as linear; however, this shape is only shown for illustration purposes and the connection elements can be curvilinear or S-shaped or any other shape encompassed by the invention. The embodiments shown here can apply to both the first and second connection elements. The cylindrical axis of the scaffold is shown as well. The connection element 220 can be attached to the valley of one undulation, 221, and the peak of another undulation, 222 (FIG. 15A). Alternatively, the connection elements 224 can be attached on either side of the valley or peak of two undulations 223, 225 (FIG. 15B). The connection element 227 can be attached to the valleys 226, 228 of two undulations (FIG. 15C). The connection element 230 can also be attached to the peak 229, and valley 231 of two undulations (FIG. 15D). The connection element 234 can also be attached to the ascending portions 232, 235 of two undulations (FIG. 15E). The figures shown here illustrate the connection element attached to an opposing undulation; however, the connection element can be attached to undulations that are shifted radially with respect to the cylindrical axis (FIG. 16) (236-238).

The proximal and distal ends of the scaffold can be labeled with respect to the heart with the proximal end closest to the aortic valve. The terms peak and valley are arbitrarily defined with respect to the proximal and distal ends of the scaffold.

Figure 17B:
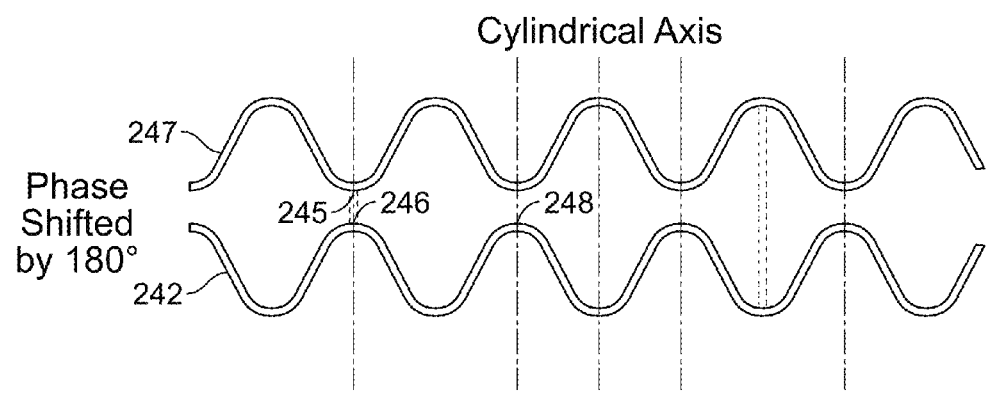

FIGS. 17A1, 17A2 and 17B show an example of phasing in adjacent circumferential elements. In FIG. 17A1, the circumferential elements 239, 240 are in-phase with each other (compare cylindrical axial lines for 243 and 244). In FIG. 17A2, the circumferential elements 239, 250 are partially out of phase. In contrast, in FIG. 17B, the circumferential elements 242, 247 are 180° out-of-phase with each other (compare 245 and 248).

Figure 18:
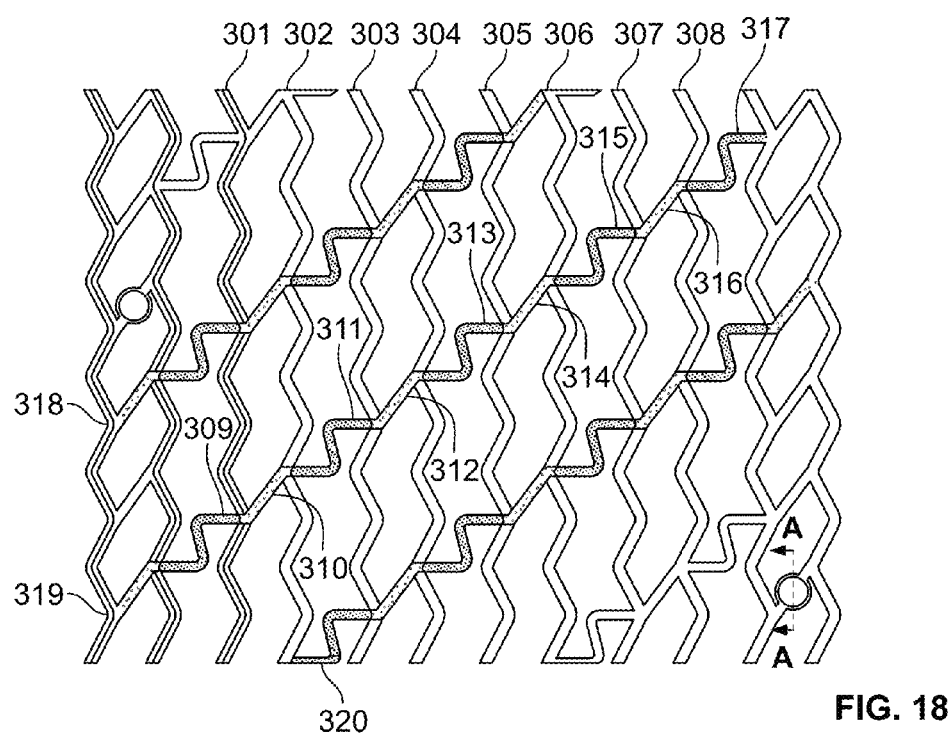
FIG. 18 shows a cut pattern of another embodiment of the scaffold where there are three first connection elements between two circumferential elements.

FIG. 18 shows a cut pattern of another embodiment of the scaffold. The circumferential elements are labeled 301-308, with the pairs of circumferential elements being shown as 301, 302; 303, 304; 305, 306; and 307, 308. The spiral pattern is shown as 309-317 and comprises an alternating pattern of connection elements between pairs of circumferential elements (second connection elements), 309, 311, 313, 315 and 317, with connection elements between the circumferential elements forming a pair (first connection elements), 310, 312, 314 and 316. The scaffold shown in the figure contains more than one spiral pattern, 318-320.

Figure 19A:
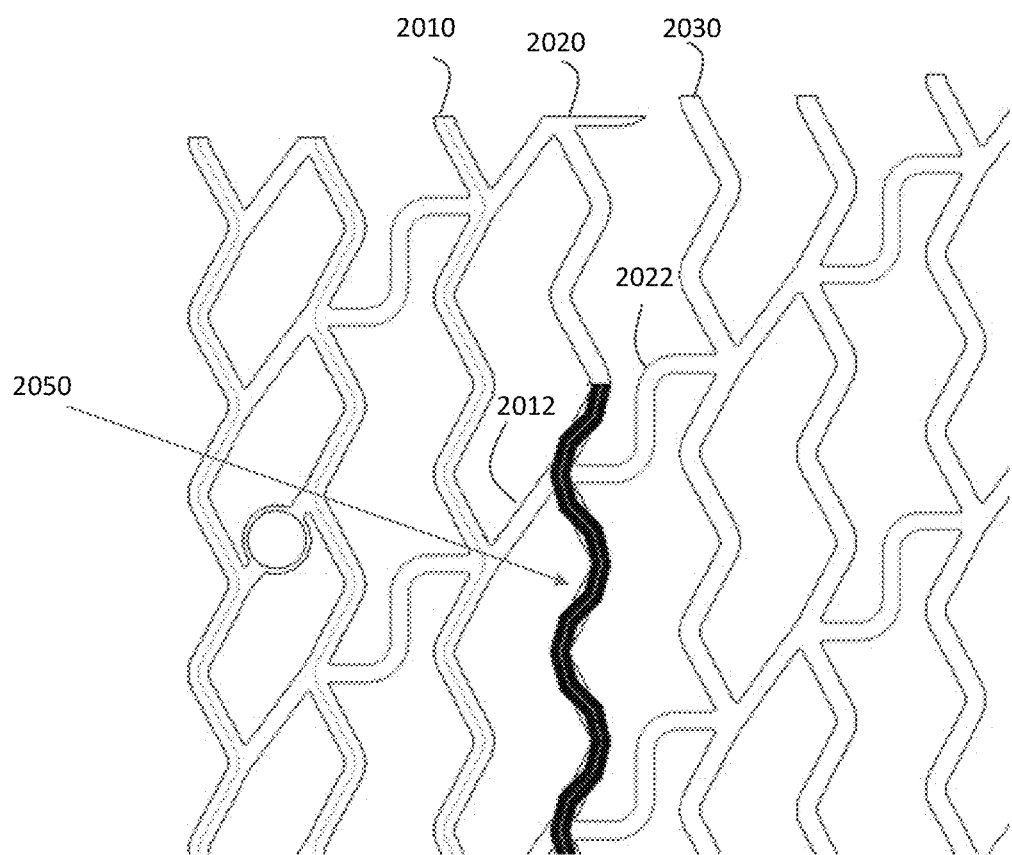
FIG. 19A schematically depicts a scaffold according to one embodiment of the present invention where a circumferential element contains a corrugated pattern composed of multiple linear segments.

FIG. 19A schematically depicts a cut view of a scaffold according to one embodiment of the present invention. The scaffold includes three longitudinally adjacent circumferential elements 2010, 2020, and 2030, where a pair of circumferential elements 2010 and 2020 are connected by first connection elements 2012, which are straight, and the circumferential elements 2020 and 2030 are connected by second connection elements 2022, which are S-shaped. The circumferential elements 2010 and 2030 are illustrated to include a sawtooth undulation pattern, which is composed of multiple linear elements. The circumferential element 2020 can include a corrugated pattern 2050 (the shaded/darker portion), which is further illustrated below in connection with FIG. 19B. For illustrative purpose, the corrugated pattern 2050 is superimposed on a phantom sawtooth pattern in FIG. 19A.

Figure 19B:
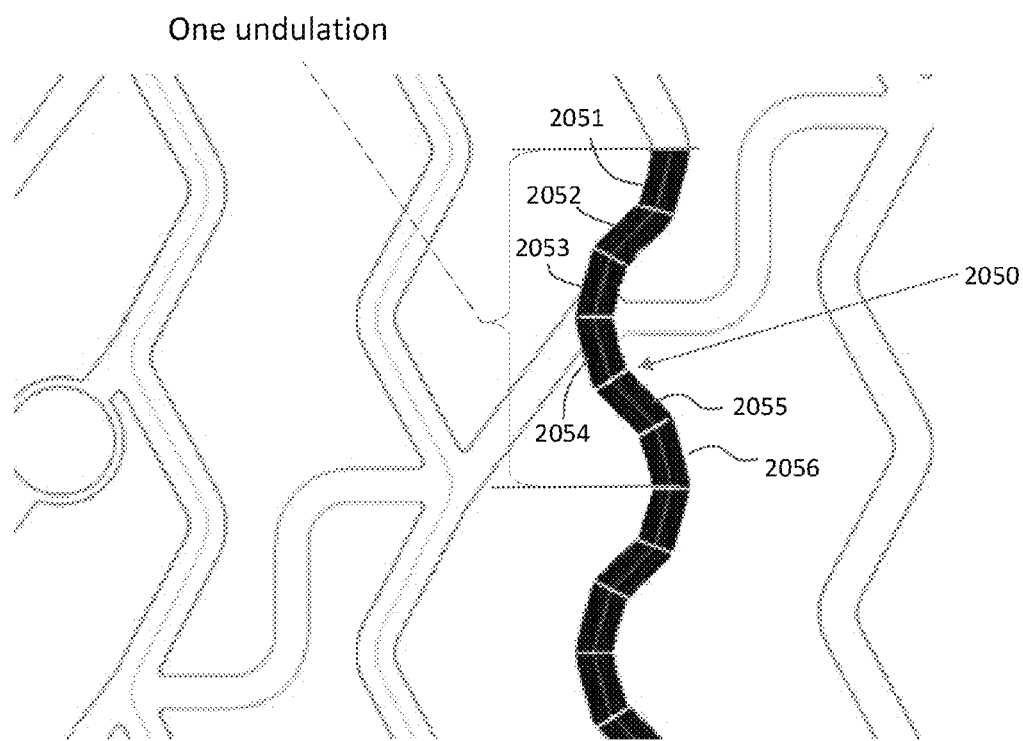
FIG. 19B is a close-up view of the scaffold depicted in FIG. 19A.

FIG. 19B is a close-up view of a portion of FIG. 19A, which further illustrates the detailed structure of the corrugated pattern 2050. In the corrugated pattern 2050 as depicted in FIG. 19B, each undulation (i.e., a repeat unit of the undulation pattern of the circumferential element, containing one peak and its adjacent valley) includes a number of linear segments, 2051, 2052, 2053, 2054, 2055, 2056, serially connected to one another. When the scaffold is in an expanded state, each of the linear segments is not collinear with an adjacent connected linear segment. The linear segments within one undulation collectively approximate a period of a sinusoidal wave.

Figure 19C:
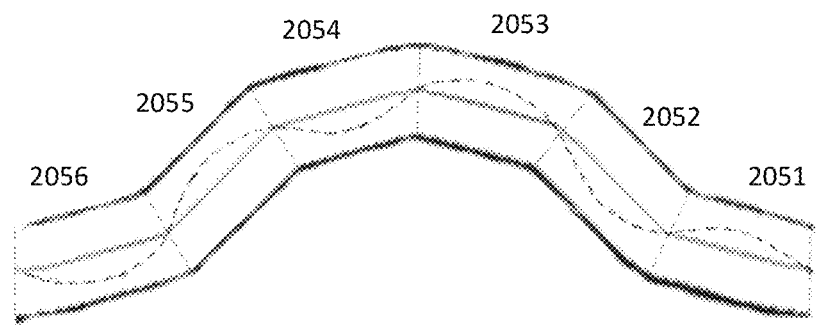
FIG. 19C schematically depicts the corrugated pattern shown in FIGS. 19A and 19B.
Figure 19D:
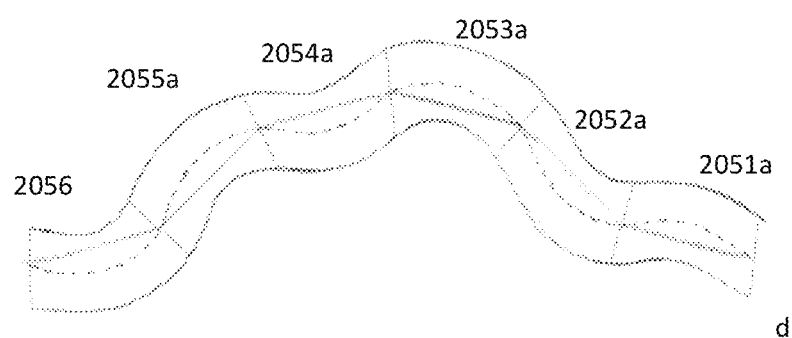
FIG. 19D schematically depicts a corrugated pattern composed of multiple curvilinear segments.

While the corrugated pattern is shown in FIGS. 19A and 19B to include 6 linear segments per undulation, a greater number of segments per undulation can also be used, e.g., 8, 10, 12, 16, 20, 24, 32, 36, 48, 64, etc. Each of the linear segments may be approximately the same length (variation<10%), or can vary in length as desired or needed. A series of connected curvilinear segments can also be used to form the corrugated pattern. For example, each undulation of the scaffold includes a series of sub-undulations or wavelets, as illustrated in FIG. 19D, where the six curvilinear segments that constitute an undulation are labeled 2051a, 2052a, 2053a, 2054a, 2055a, and 2056a. (FIG. 19C depicts the same corrugated pattern as shown in FIG. 19B, with the addition of an undulating central line which serves as the central line for the circumferential element shown in FIG. 19D). The number of the curvilinear segments that form the corrugated pattern can also be greater than 6, e.g., 8, 10, 12, 16, 20, 24, 32, 36, 48, 64, etc. The curvilinear segments within one undulation in FIG. 19D also collectively approximate a period of a sinusoidal wave.

Such corrugated patterns allow the scaffold, especially one made from a polymeric material capable of induced crystallization by expansion of the scaffold, to have additional local stress points, in contrast to the two local stress points in an undulation in a conventional scaffold design (which are usually at the apex of the peak and of the valley). Thus, the corrugated patterns allow the stress due to radial expansion of the scaffold to be more evenly distributed along the circumferential elements and allow for more uniform distribution of induced crystallization of the polymeric material. As a result, a scaffold including a corrugated pattern as described can have higher radial strength, reduced acute recoil after deployment, and reduced creep.

The connection elements shown in FIGS. 19A and 19B are linear or S-shaped. In other embodiments, the connection elements can also include a corrugated pattern with multiple linear segments or curvilinear segments joined together.

While FIGS. 19A and 19B illustrate a corrugated pattern in two consecutive undulations in a circumferential element 2020, in alternative embodiments, such a corrugated pattern can span the entire circumferential element 2020. In other embodiments, all of the circumferential elements can be made of repeat corrugated patterns, as illustrated in FIGS. 20-27.

Figure 20A:
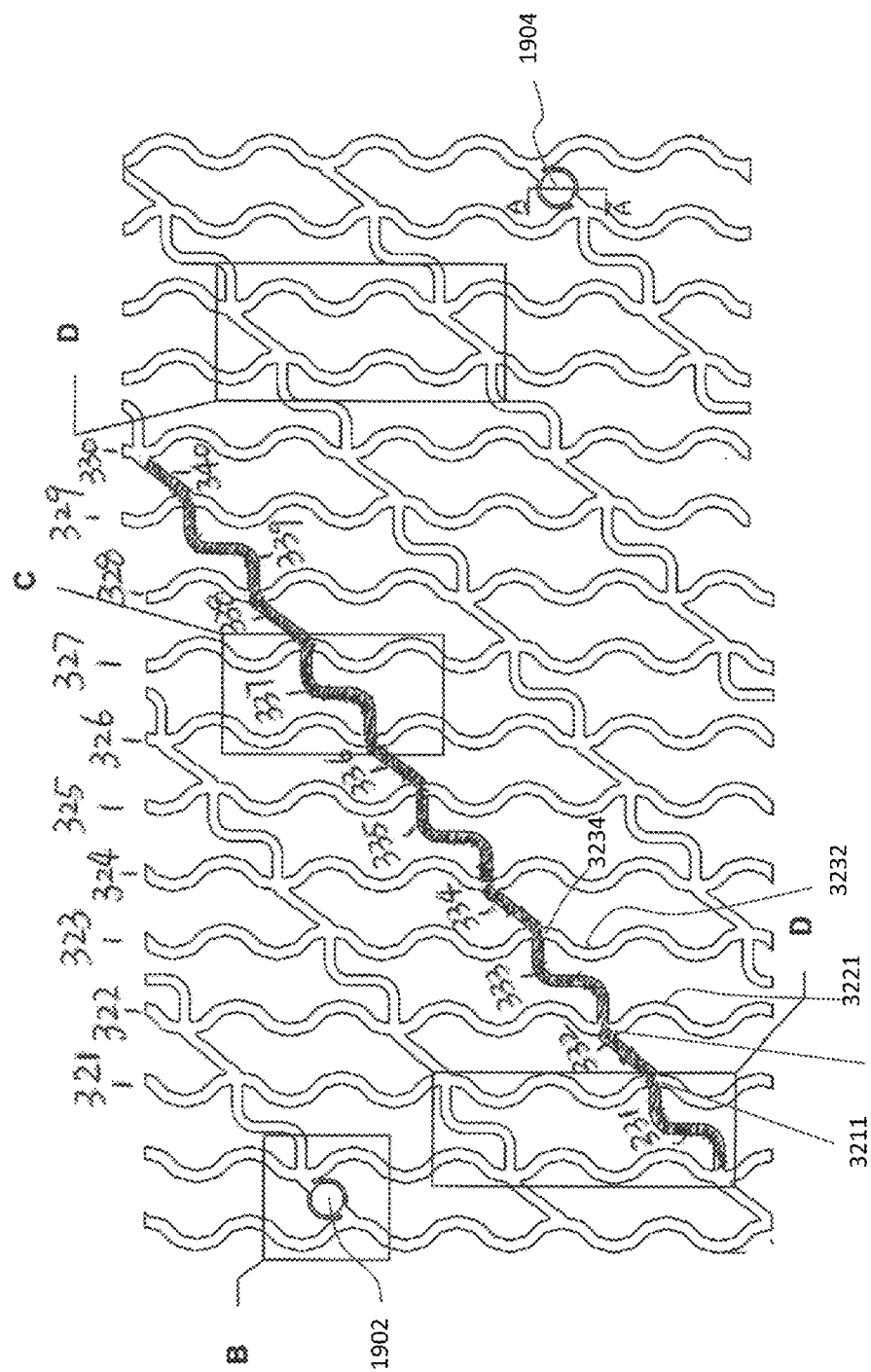
FIG. 20A shows a cut pattern according to one embodiment of the present invention that includes the corrugated pattern shown in FIGS. 19A-19B.
Figure 20E:
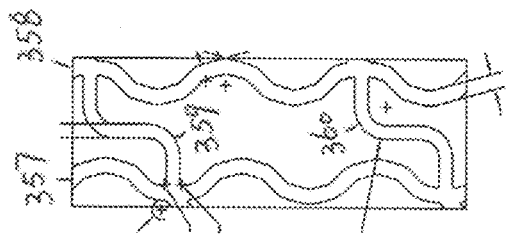
FIGS. 20B-20E show detailed views of parts of the scaffold in FIG. 20A.

FIG. 20A shows an embodiment of a scaffold of the present invention where each circumferential element is composed of repeated corrugated patterns. The circumferential elements are labeled 321-330, with the pairs of circumferential elements being shown as 321, 322; 323, 324; 325, 326; 327, 328 and 329, 330. The peaks and valleys of the scaffold may be generally in phase. Three connection elements are used between each two longitudinally adjacent circumferential elements, one per two undulations on each circumferential element. The pair of longitudinally adjacent circumferential elements 321, 322 are connected by a straight (or linear) first circumferential element 332; and the pair of longitudinally adjacent circumferential elements 322, 323 are connected by an S-shaped second circumferential element 333. The first connection element 332 connects a peak 3211 of the circumferential element 321 with a valley 3222 of the circumferential element 322. The second connection element 333 connects the valley 3222 with a peak 3234 of the circumferential element 323 that is adjacent to a valley 3232 (the valley 3232 is longitudinally aligned with the valley 3222). The above connection pattern repeats across the stent and forms a spiral which includes the connection elements 331-340. Two marker dots 1902 and 1904 are located at each end of the scaffold (on a connection element between the first pair circumferential elements and the last pair of circumferential elements).

Figure 20D:
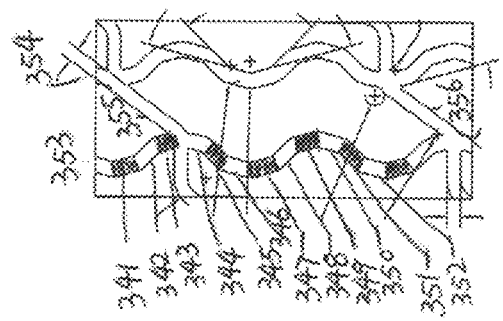

Detailed views of portions of the scaffold in FIG. 20A are shown in FIGS. 20B-20E. In FIG. 20D, a close-up view of a portion of FIG. 20A is shown to further illustrate repeated corrugated patterns. In this embodiment, two longitudinally adjacent circumferential elements are shown as 353, 354. They are connected by connection elements (first connection elements) 355 and 356. The linear segments that constitute the repeated corrugated patterns are shown as 341-352.

Figure 20F:
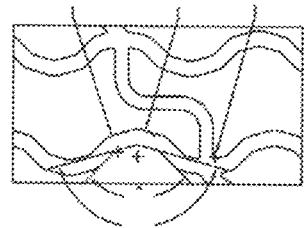
FIG. 20F shows the cross section of the marker dot in FIG. 20A.
Figure 20B:
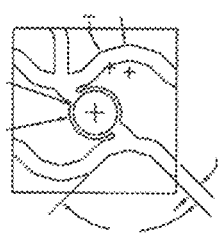
Figure 20C:
Figure 20G:
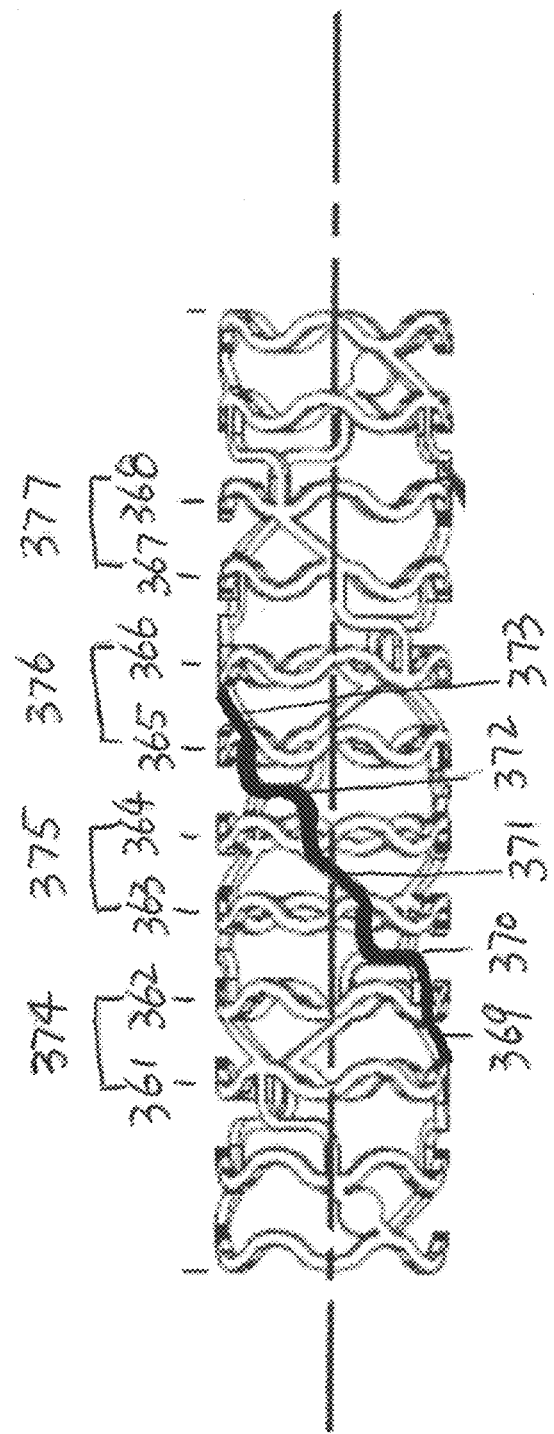
FIG. 20G shows a side view of the scaffold in FIG. 20A.

FIG. 20F shows a cross section view of the marker dot 1904, which takes a cup shape with a depression in the center to accommodate a radiopaque marker. FIG. 20G is a side view of the scaffold shown in FIG. 20A. The circumferential elements are labeled 361-368, forming pairs 374-377. The connection elements between circumferential elements within a pair (first connection element) are shown as 369, 371, 373, while the connection element between two pairs of circumferential elements are labeled 370, 372. A spiral is formed by connection elements 369-373.

Figure 21A:
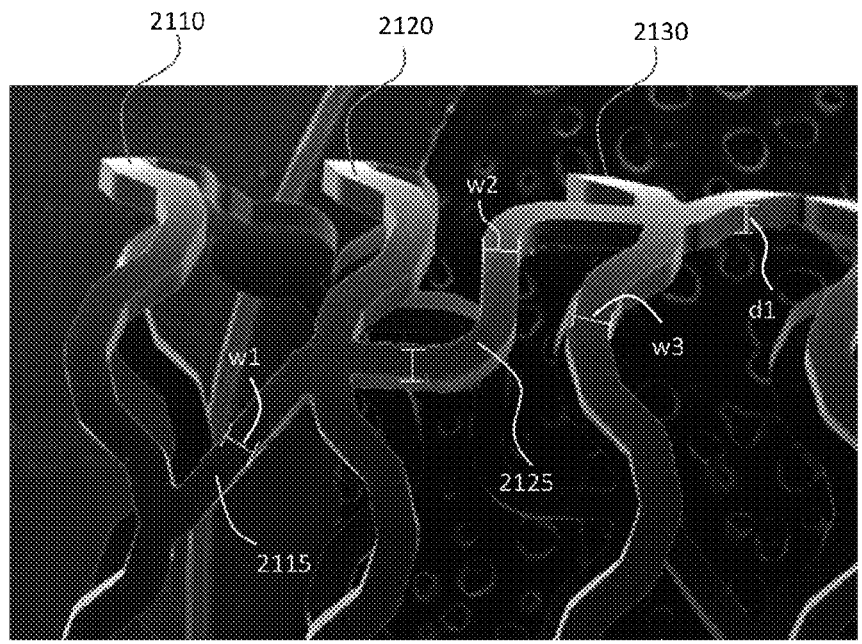
FIGS. 21A-21C depict three-dimensional side views of a portion of an expanded scaffold according to one embodiment of the present invention that includes the corrugated pattern shown in FIGS. 19A-19B.
Figure 21B:
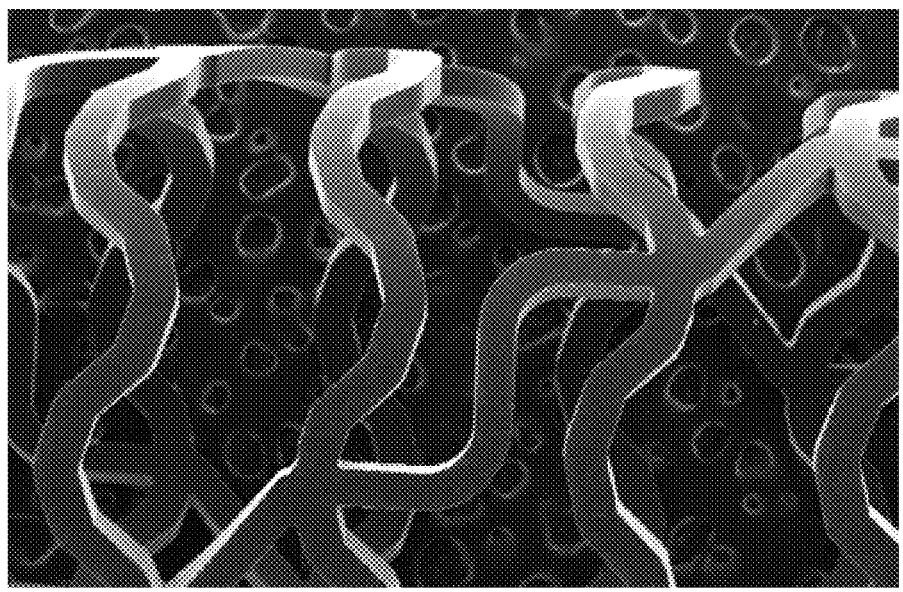
Figure 21C:
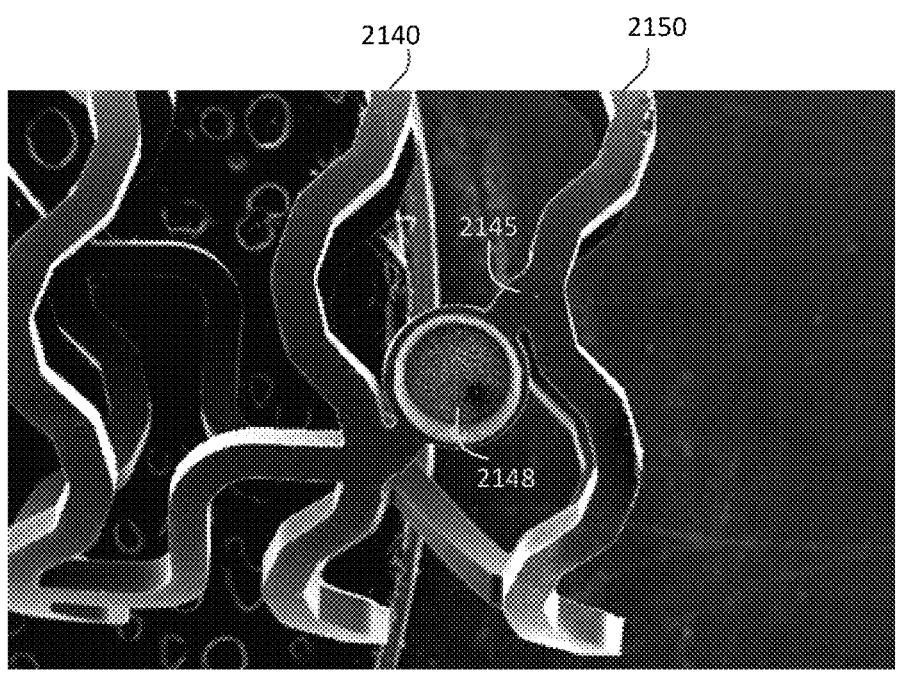

FIG. 21A shows a three-dimensional side view of a portion of an expanded scaffold according to one embodiment of the present invention that includes the corrugated pattern described in connection with FIGS. 19A-19B. Three longitudinally adjacent circumferential elements are shown, 2110, 2120 and 2130. Circumferential elements 2110 and 2120 are connected by a straight first connection element 2115. Circumferential elements 2120 and 2130 are connected by an S-shaped second connection element 2125. Exemplary dimensions of various elements of the scaffold can be as follows: the width of the first connection element w1 can be about 100-200 μm, e.g., 140-160 μm; the thickness of the first connection element d1 can be about 100-200 μm, e.g., 120-150 μm; the width of the S-shaped second connection element 2125 w2 can be about 100-200 μm, e.g., 150-180 μm; the width of the linear segment constituting the corrugated pattern w3 can be about 100-250 μm, e.g., 160-200 μm as shown. FIG. 21B is a three-dimensional side view of another portion the expanded scaffold depicted in FIG. 21A. FIG. 21C is yet another three-dimensional view of the expanded scaffold depicted in FIG. 21A, showing a marker dot 2148 located in the middle of a connection element 2145 which connects two circumferential elements 2140 and 2150 located at one longitudinal end of the scaffold. The marker dot can take a cup configuration as shown in FIG. 19F.

Figure 22A:
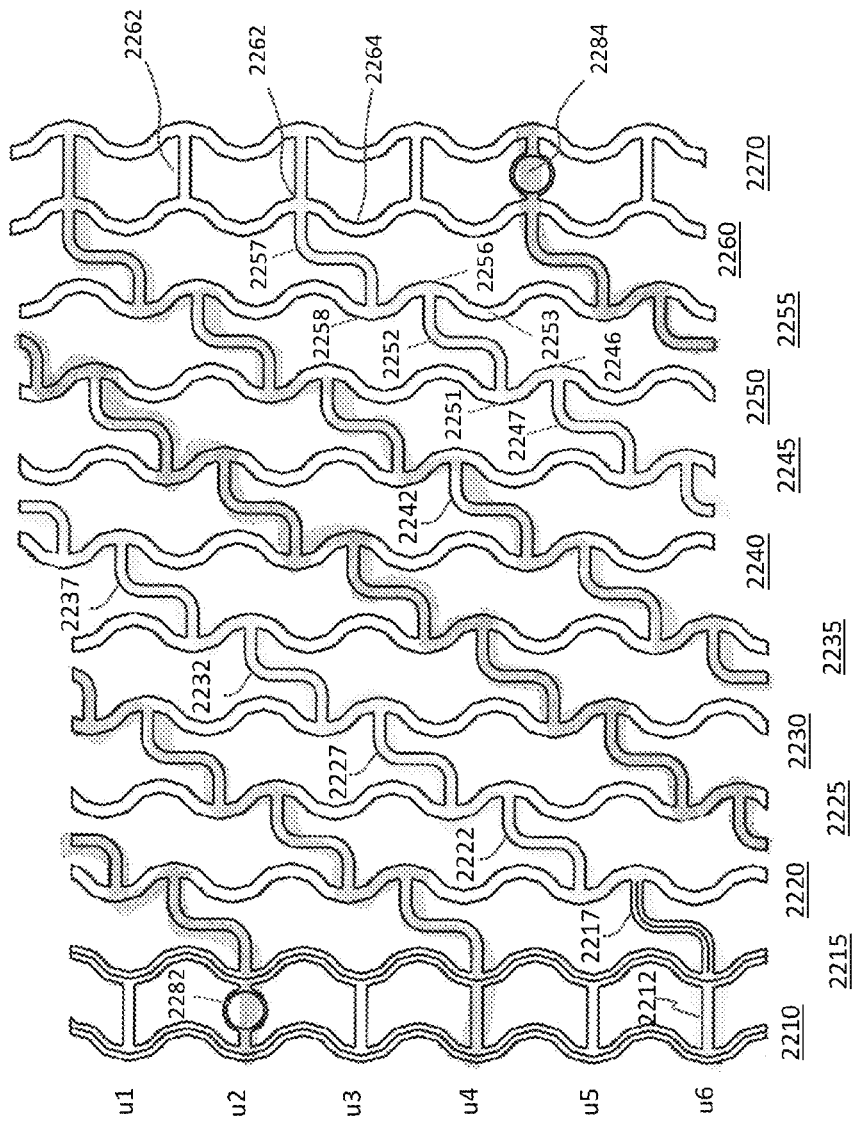
FIG. 22A depicts a cut pattern of a scaffold according to one embodiment of the present invention that includes the corrugated pattern shown in FIGS. 19A-19B.

FIG. 22A shows a cut pattern of a scaffold according to one embodiment of the present invention where each circumferential element is composed entirely of the corrugated pattern described in connection with FIGS. 19A-19B. The scaffold includes circumferential elements 2210, 2215, 2220, 2225, 2230, 2235, 2240, 2245, 2250, 2255, 2260, 2265, and 2270. Each circumferential element includes 6 undulations (u1, u2, u3, u4, u5, u6, as shown), and the alternating peaks and valleys of these circumferential elements are all generally in phase. Each two longitudinally adjacent circumferential elements among 2215, 2220, 2225, 2230, 2235, 2240, 2245, 2250, 2255, 2260, 2265 are in turn connected by S-shaped connection elements 2217, 2222, 2227, 2232, 2237, 2242, 2247, 2252, 2257 valley to peak for every other valley on the circumferential elements.

The amplitude of the undulations for each of the circumferential elements can be the same of different. The S-shaped connection elements 2217, 2222, 2227, 2232, 2237, 2242, 2247, 2252, 2257 can also vary in length. In one embodiment, the amplitude of the undulations of two longitudinally adjacent circumferential elements and an S-shaped connection element disposed therebetween can be designed such when the stent is crimped, the S-shaped connection element can be positioned within the contours of the undulations without having to bend out of the tubular surface formed by the circumferential elements.

The circumferential elements 2210 and 2215 at a proximal end of the scaffold may be connected by straight connection elements 2212 valley to valley for each undulation. The proximal pair of circumferential elements 2210 and 2215 together with the connection elements 2212 form a proximal end zone. The circumferential elements 2260 and 2270 at the distal end of the scaffold may be connected by straight connection elements 2262 peak to peak for each undulation. The circumferential elements 2260 and 2270 together with the connection elements 2262 form a distal end zone. While the proximal end zone and the distal end zone are both shown to include two circumferential elements that are generally in phase, either or both of the zones can alternatively include two circumferential elements that are phase shifted, e.g., 180 degree out of phase, such as those embodiments illustrated in FIG. 25A and FIG. 26A. Marker dots 2282 and 2284 are each located on a connection element connecting the proximal pair of circumferential elements 2210 and 2215 and a connection element connecting the distal pair of circumferential elements 2260 and 2270, respectively.

In the scaffold as shown in FIG. 22A, the connection elements between adjacent circumferential elements and portions of the circumferential elements form spiral patterns that cut across the scaffold. To illustrate, for longitudinally adjacent circumferential elements 2250, 2255, the connection element 2252 connects the valley 2251 and the peak 2256 which is adjacent to the valley 2253 (the valley 2253 is longitudinally aligned with valley 2251). Similarly, for longitudinally adjacent circumferential elements 2255, 2260, the connection element 2257 connects the valley 2258 and the peak 2261 which is adjacent to the valley 2264 (the valley 2264 is longitudinally aligned with the valley 2258). Thus, the connection element 2247, a portion of circumferential element 2250 between the peak 2246 and the valley 2251, the connection element 2252, a portion of circumferential element 2255 between the peak 2256 and the valley 2258, then the connection element 2258, form a contiguous spiral.

Figure 22B:
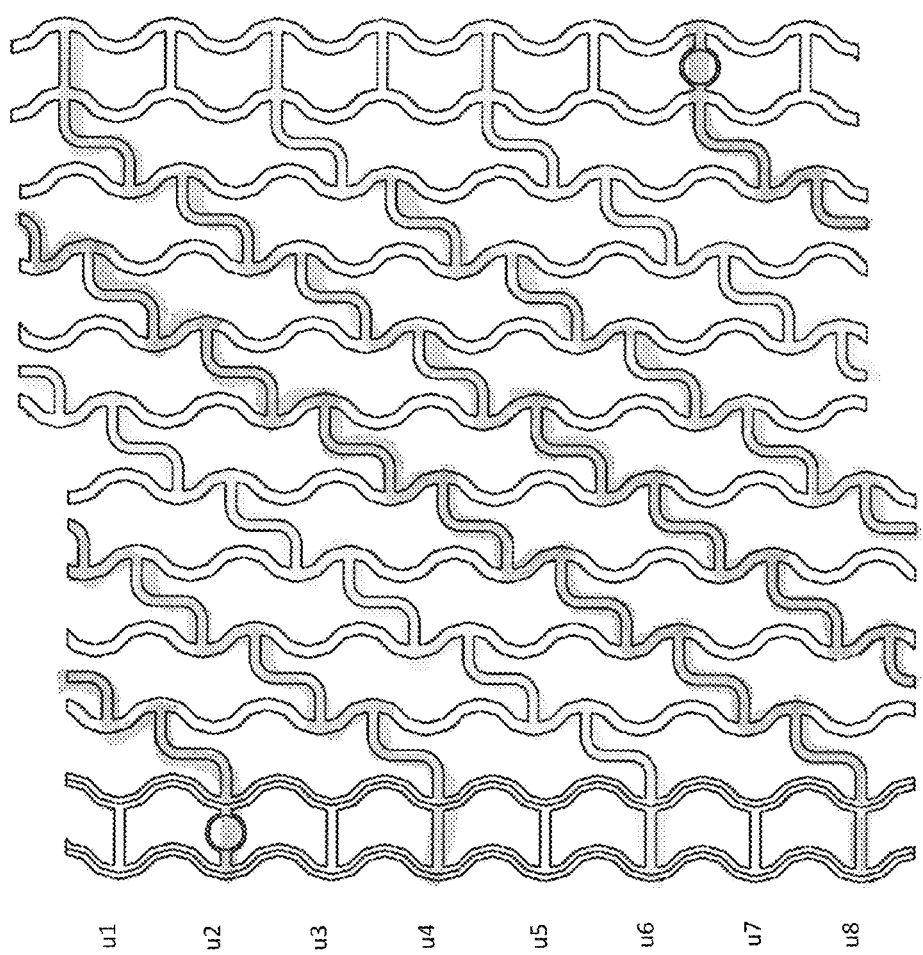
FIG. 22B depicts a cut pattern of a scaffold according to another embodiment of the present invention that includes the corrugated pattern shown in FIGS. 19A-19B.

FIG. 22B shows a cut pattern of a scaffold according to another embodiment of the present invention where each circumferential element is composed entirely of the corrugated pattern described in connection with FIGS. 19A-19B. This cut pattern is substantially the same as the pattern depicted in FIG. 22A with the exception that each circumferential element in this pattern includes 8 undulations (u1, u2, u3, u4, u5, u6, u7, u8, as shown) instead of 6 undulations as shown in FIG. 22A.

Figure 23:
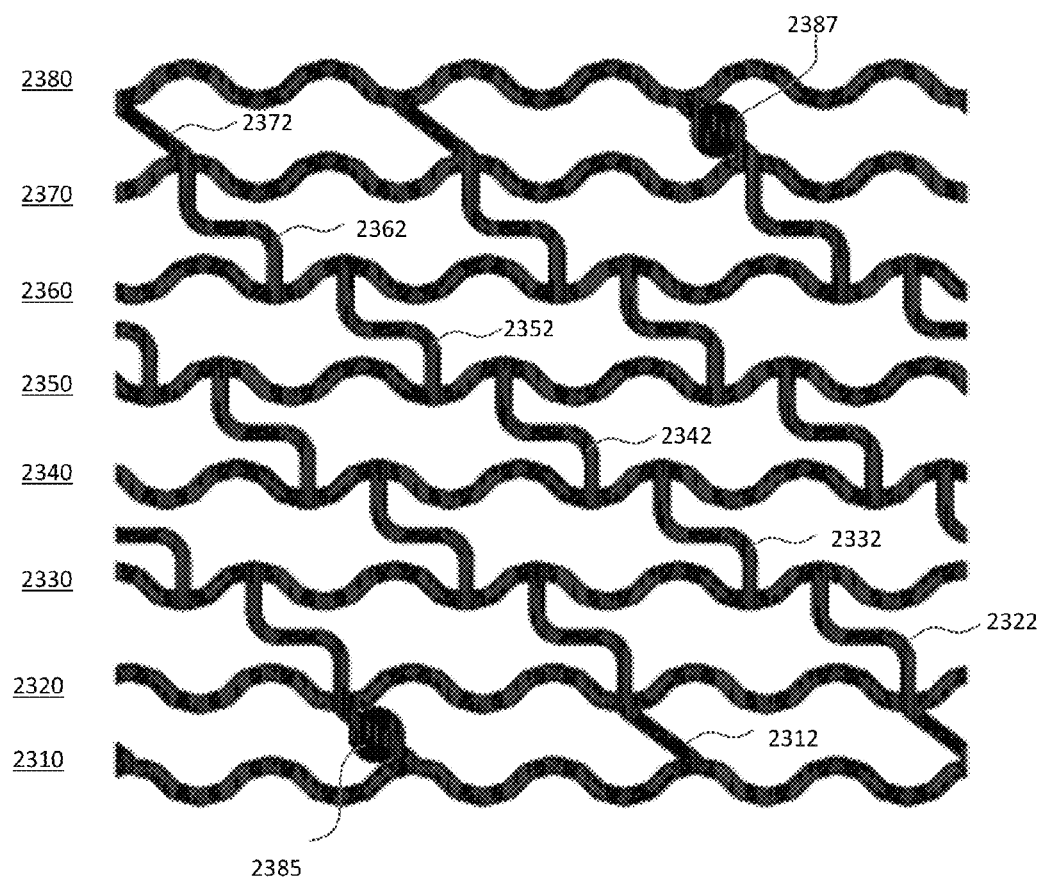
FIG. 23 depicts a cut pattern of a scaffold according to another embodiment of the present invention that includes the corrugated pattern shown in FIGS. 19A-19B.

FIG. 23 shows a cut pattern of a scaffold according to another embodiment of the present invention that includes the corrugated pattern described in connection with FIGS. 19A-19B. The scaffold includes circumferential elements 2310, 2320, 2330, 2340, 2350, 2360, 2370, 2380, which are in turn connected by connection elements 2312, 2322, 2332, 2342, 2352, 2362, 2372. The design pattern between circumferential element 2300 and 2370 are similar to the pattern in FIG. 22, between circumferential elements 2200 to 2255 in terms of the connection patterns (S-shaped connection elements connecting adjacent pair of circumferential elements peak to valley). A proximal pair of circumferential elements 2310 and 2320 may be connected by diagonal straight connection elements 2312 (valley to peak). A distal pair of circumferential elements 2370 and 2380 may be connected by diagonal straight connection elements 2372 (valley to peak). Marker dots 2385 and 2387 are each located on a connection element connecting the proximal pair of circumferential elements 2310 and 2320 and a connection element connecting the distal pair of circumferential elements 2370 and 2380, respectively.

Figure 24:
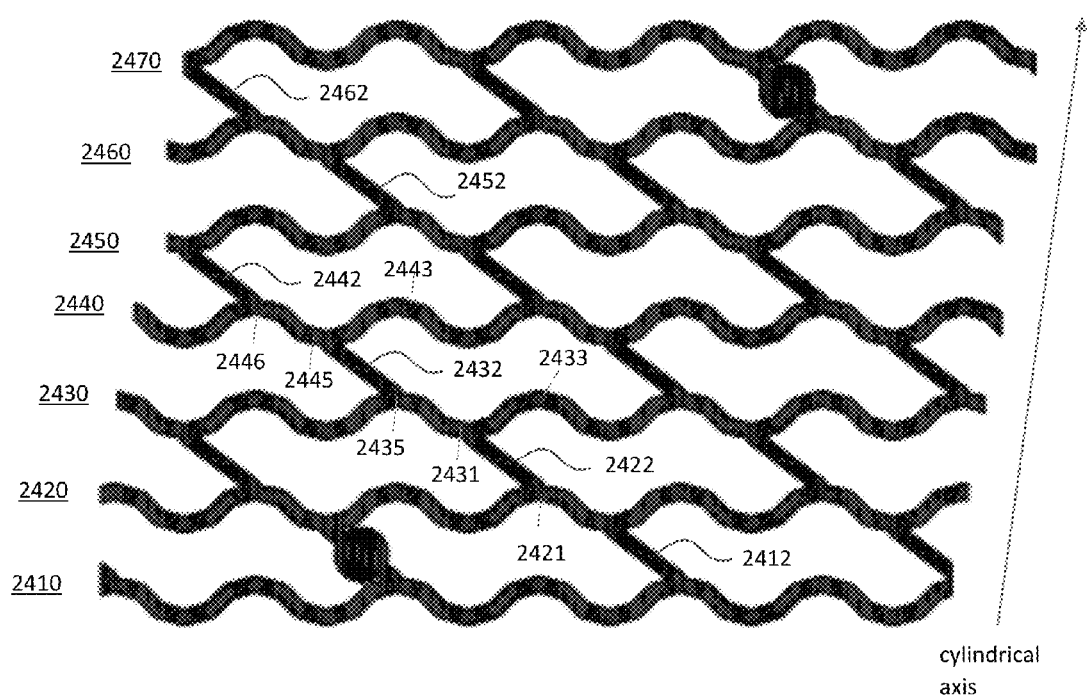
FIG. 24 depicts a cut pattern of a scaffold according to another embodiment of the present invention that includes the corrugated pattern shown in FIGS. 19A-19B.

FIG. 24 shows a cut view of a scaffold according to another embodiment of the present invention that includes the corrugated pattern described in connection with FIGS. 19A-19B. The scaffold includes circumferential elements 2410, 2420, 2430, 2440, 2450, 2460, 2470, which are in turn connected by connection elements 2412, 2422, 2432, 2442, 2452, 2462. Each circumferential element includes 6 undulations, and the alternating peaks and valleys of these circumferential elements are all generally in phase with respect to the cylindrical axis. Each two longitudinally adjacent circumferential elements are connected peak to valley by diagonal linear connection elements for every other peak (or valley) on the circumferential elements. The connection elements are all substantially parallel to each other, and together with portions of the circumferential elements form spiral patterns that cut across the scaffold. To illustrate, for longitudinally adjacent circumferential elements 2420, 2430, the connection element 2422 connects the peak 2421 and the valley 2431 which is adjacent to the peak 2433 (which is longitudinally aligned with the valley 2421). Similarly, for longitudinally adjacent circumferential elements 2430, 2440, the connection element 2432 connects the peak 2435 and the valley 2445 which is adjacent to the peak 2443 that is longitudinally aligned with the peak 2435. Thus, the connection element 2422, a portion of circumferential element 2430 between the valley 2431 and the peak 2435, the connection element 2432, a portion of circumferential element 2440 between the valley 2445 and the peak 2446, then the connection element 2242, form a contiguous spiral.

Figure 25A:
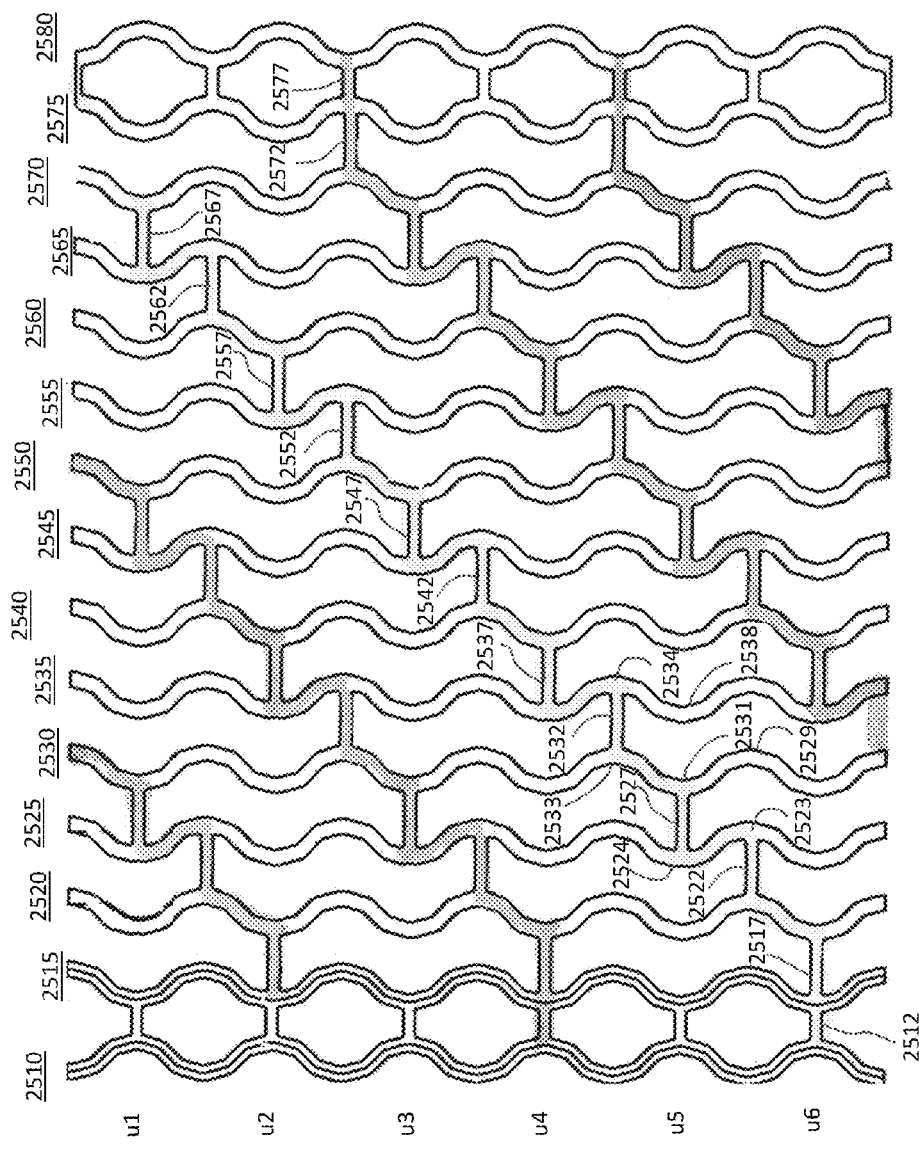
FIG. 25A depicts a cut pattern of a scaffold according to another embodiment of the present invention that includes the corrugated pattern shown in FIGS. 19A-19B.

FIG. 25A shows a cut pattern of a scaffold according to another embodiment of the present invention where each circumferential element is composed entirely of the corrugated pattern described in connection with FIGS. 19A-19B. The scaffold includes circumferential elements 2510, 2515, 2520, 2525, 2530, 2535, 2540, 2545, 2550, 2555, 2560, 2565, 2570, 2575, 2580, which are in turn connected by connection elements 2512, 2517, 2522, 2527, 2532, 2537, 2542, 2547, 2552, 2557, 2562, 2567, 2572, 2577. Each circumferential element includes 6 undulations (u1, u2, u3, u4, u5, u6, as shown), and the alternating peaks and valleys of these circumferential elements are all generally in phase except the first circumferential element 2510 and the last circumferential element 2580, which are 180 degree out of phase with (or opposing) the remaining circumferential elements. Except the first two circumferential elements 2510, 2515 and the last two circumferential elements 2575, 2580, which may be connected peak to valley by longitudinally aligned linear connection elements 2512 and 2577 for each undulation, each of the remaining longitudinally adjacent circumferential element pairs may be connected by longitudinally aligned linear connection elements valley to valley (or peak to peak) every two undulations. The proximal pair of circumferential elements 2510 and 2515 together with the connection elements 2512 form a proximal end zone. The distal pair of circumferential elements 2575 and 2580 together with the connection elements 2577 form a distal end zone. While the proximal end zone and the distal end zone are both shown to include two circumferential elements that are generally 180 degree out of phase (or opposing to each other), either or both of the zones can alternatively include two circumferential elements that are generally in phase, such as the embodiment illustrated in FIG. 22A.

In the scaffold as shown in FIG. 25A, the connection elements together with portions of the circumferential elements form spiral patterns that cut across the scaffold. To illustrate, for longitudinally adjacent circumferential elements 2525, 2530, the connection element 2527 connects the valley 2524 and the valley 2531 which is adjacent to the peak 2529 (the peak 2529 is longitudinally aligned with the peak 2523). Similarly, for longitudinally adjacent circumferential elements 2530, 2535, the connection element 2532 connects the peak 2533 and the peak 2534 which is adjacent to the valley 2538 (the valley 2538 is longitudinally aligned with the valley 2531). Thus, the connection element 2527, a portion of circumferential element 2530 between the valley 2431 and the peak 2435, the connection element 2432, a portion of the circumferential element 2440 between the valley 2531 to the peak 2533, then the connection element 2532, form a contiguous spiral (which continues on to include connection elements 2537, 2542, 2547, 2552, 2557, 2562, 2567, as well as the portions between the peak and its adjacent valley on each of the circumferential elements where the circumferential elements intersect the connection elements.

Figure 25B:
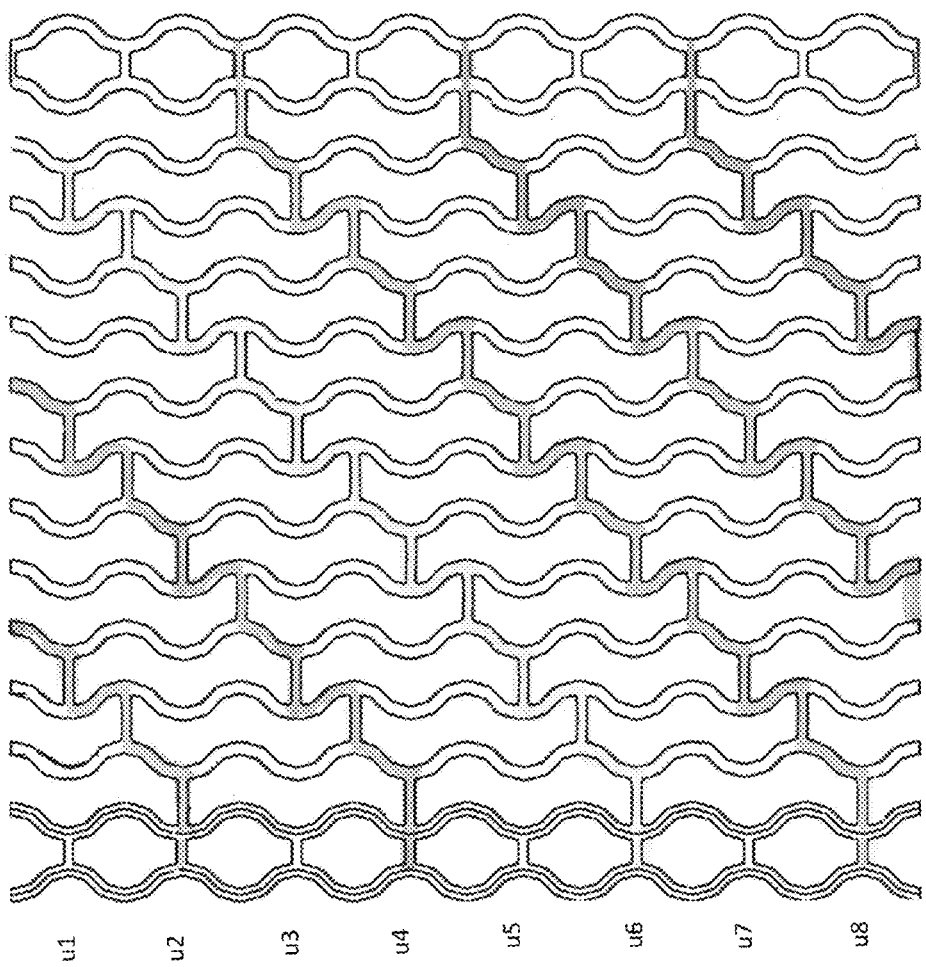
FIG. 25B depicts a cut pattern of a scaffold according to another embodiment of the present invention that includes the corrugated pattern shown in FIGS. 19A-19B.

FIG. 25B shows a cut pattern of a scaffold according to another embodiment of the present invention where each circumferential element is composed entirely of the corrugated pattern described in connection with FIGS. 19A-19B. This cut pattern is substantially the same as the pattern depicted in FIG. 25A with the exception that each circumferential element in this pattern includes 8 undulations (u1, u2, u3, u4, u5, u6, u7, u8, as shown) instead of 6 undulations as shown in FIG. 22A.

Figure 26A:
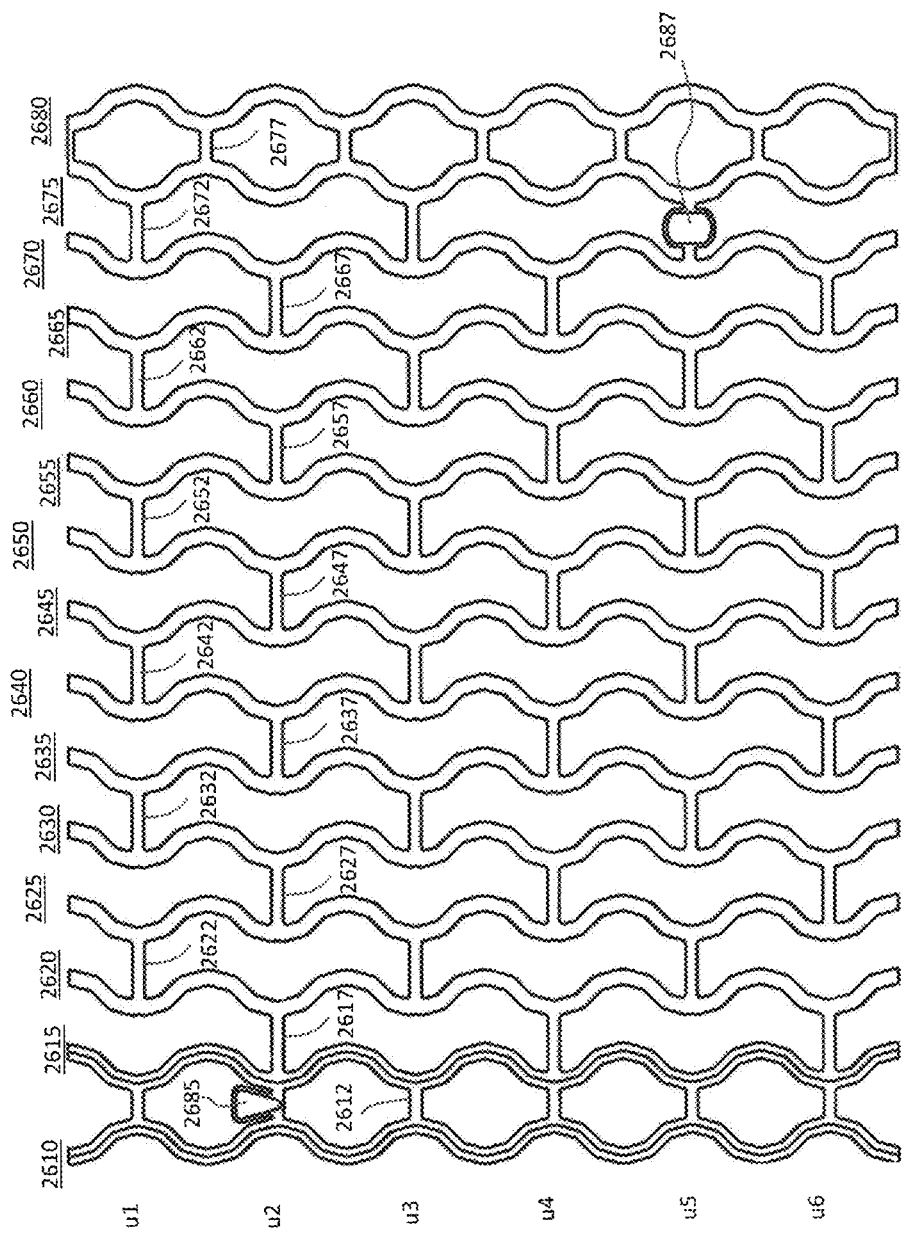
FIG. 26A depicts a cut pattern of a scaffold according to another embodiment of the present invention that includes the corrugated pattern shown in FIGS. 19A-19B.

FIG. 26A shows a cut pattern of a scaffold according to another embodiment of the present invention where each circumferential element is composed entirely of the corrugated pattern described in connection with FIGS. 19A-19B. The scaffold includes circumferential elements 2610, 2615, 2620, 2625, 2630, 2635, 2640, 2645, 2650, 2655, 2660, 2665, 2670, 2675, 2680, which are in turn connected by connection elements 2612, 2617, 2622, 2627, 2632, 2637, 2642, 2647, 2652, 2657, 2662, 2667, 2672, 2677. Each circumferential element includes 6 undulations (u1, u2, u3, u4, u5, u6, as shown), and the alternating peaks and valleys of these circumferential elements are all generally in phase except the first circumferential element 2610 and the last circumferential element 2680, which are 180 degree out of phase with (or opposing) the remaining circumferential elements. Except the first two circumferential elements 2610, 2615 and the last two circumferential elements 2675, 2680, which are connected peak to valley by longitudinally aligned linear connection elements 2612 and 2617 respectively for each undulation, each of the remaining longitudinally adjacent circumferential element pairs are connected by longitudinally aligned linear connection elements valley to valley (or peak to peak) every two undulations. The proximal pair of circumferential elements 2610 and 2615 together with the connection elements 2612 form a proximal end zone. The distal pair of circumferential elements 2675 and 2680 together with the connection elements 2677 form a distal end zone. While the proximal end zone and the distal end zone are both shown to include two circumferential elements that are generally 180 degree out of phase (or opposing to each other), either or both of the zones can alternatively include two circumferential elements that are generally in phase, such as the embodiment illustrated in FIG. 22A.

Compared with the design pattern depicted in FIG. 25 where the connection elements and portions of the circumferential elements form contiguous spirals, the first connection elements of this embodiment (2617, 2627, 2637, 2647, 2657, 2667) are longitudinally aligned among themselves, the second connection elements (2612, 2622, 2632, 2642, 2652, 2662, 2672) are also longitudinally aligned among themselves, whereas the first connection elements and the second connection elements are staggered and offset for one complete undulation. Marker dots 2685 and 2687 are each located on a connection element connecting the proximal end pair of circumferential elements 2610 and 2615 and a connection element connecting the distal end pair of circumferential elements 2675 and 2680, respectively.

Figure 26B:
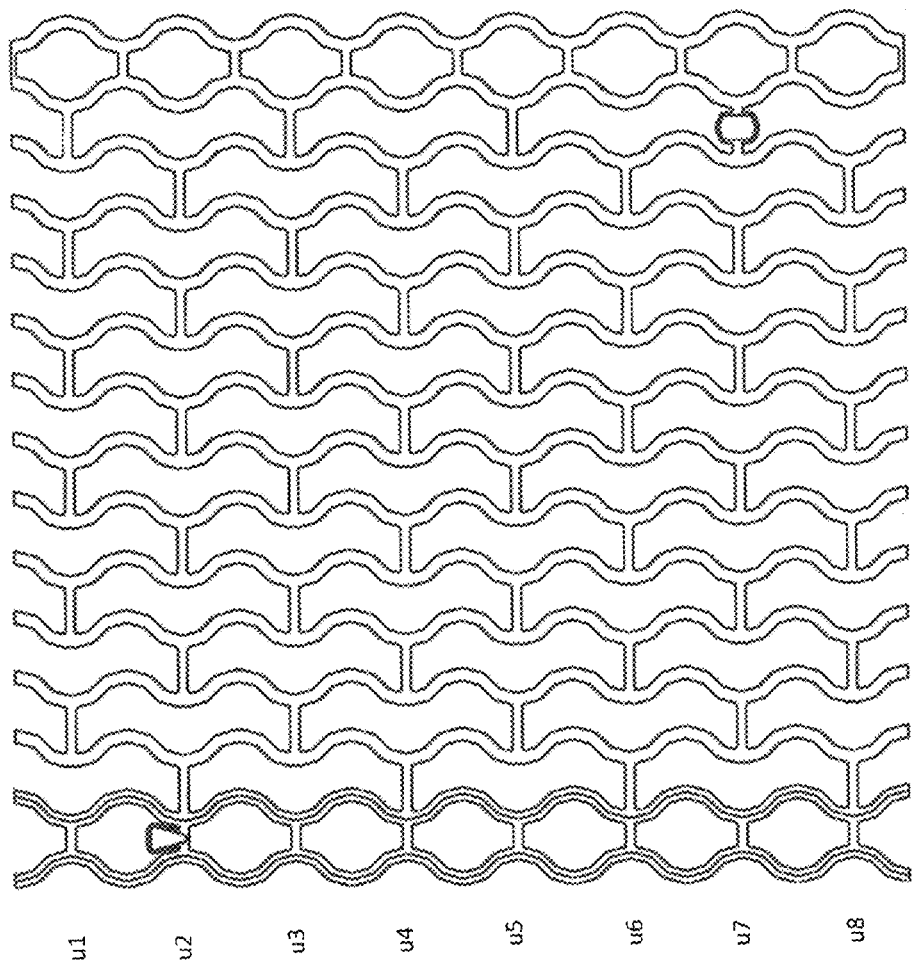
FIG. 26B depicts a cut pattern of a scaffold according to another embodiment of the present invention that includes the corrugated pattern shown in FIGS. 19A-19B.

FIG. 26B shows a cut pattern of a scaffold according to another embodiment of the present invention where each circumferential element is composed entirely of the corrugated pattern described in connection with FIGS. 19A-19B. This cut pattern is substantially the same as the pattern depicted in FIG. 26A with the exception that each circumferential element in this pattern includes 8 undulations (u1, u2, u3, u4, u5, u6, u7, u8, as shown) instead of 6 undulations as shown in FIG. 22A.

Figure 27A:
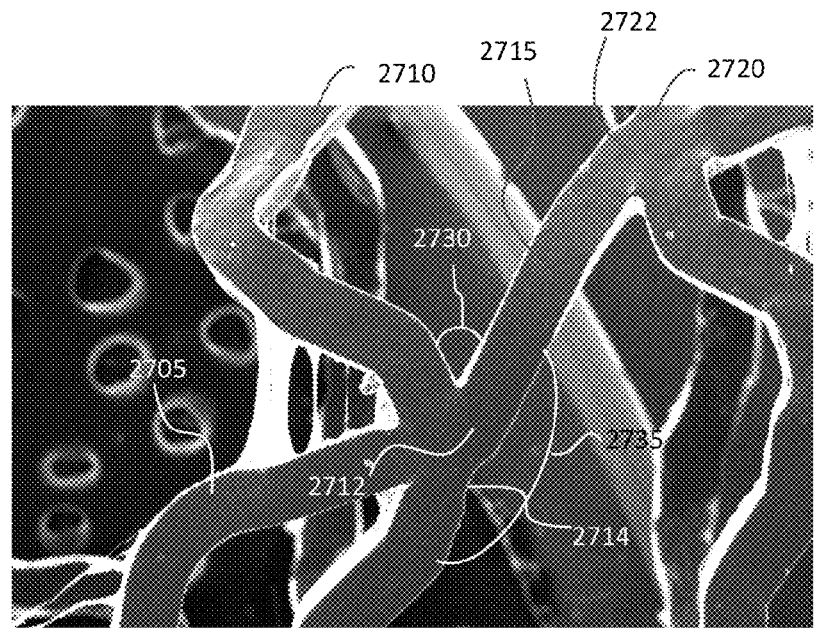
FIGS. 27A-27B show three-dimensional views of a scaffold according to an embodiment of the present invention that includes the corrugated pattern shown in FIGS. 19A-19B as well as a notch.
Figure 27B:
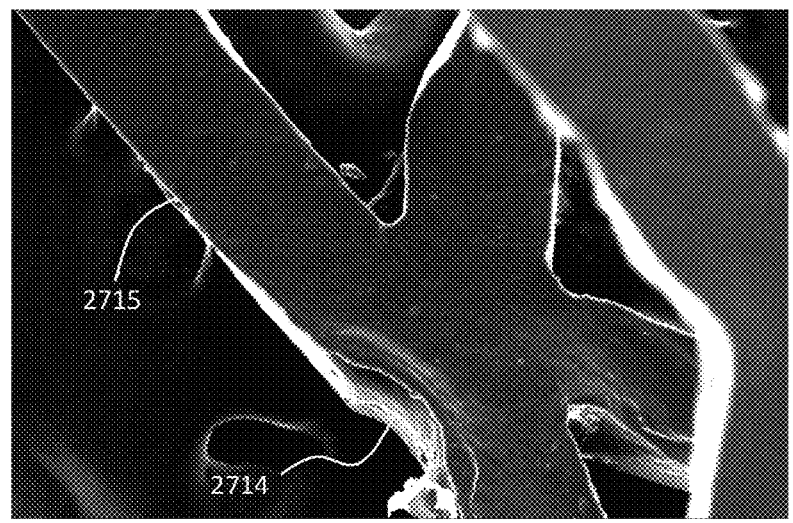

FIG. 27A is a three-dimensional view of a portion of a scaffold according to another embodiment of the present invention that includes the corrugated pattern described in connection with FIGS. 19A-19B. FIG. 27B is an enlarged back view of the scaffold depicted in FIG. 27A. Shown in FIG. 27A are two circumferential elements 2710 and 2720, connected by a linear connection element 2715 between the peak 2712 of circumferential element 2710 and a valley 2722 of the circumferential element 2720 that is 180 degree phase shifted from the peak 2712. Circumferential element 2710 is also connected to a previous circumferential element (not shown) by an S-shaped connection element 2705. Both the connection elements 2705 and 2715 join the circumferential element 2710 at the same peak 2712. The connection element 2715 and the peak 2712 join to form an angle 2730 and a larger angle 2735 opposing to the sharp angle 2730. The angle 2735 may be obtuse (greater than 90 degree and smaller than 180 degree), or greater than 180 degree. A notch is placed at the intersection of the connection element 2715 and the peak 2712 and within the angle 2735 (a notch can be a slight indentation or reduction in the thickness of the connection element or the circumferential element, and can take various shapes such as V shape, a U shape, etc.). Such a notch facilitates crimping and expansion by allowing the linear segments of the corrugated pattern to fold with reduced fatigue or buckling at the point of folding or crimping. A notch can also be placed on both sides of a circumferential element, and can be placed in other points along a circumferential element where the connection elements and the circumferential element intersect. Notches can also be distributed in any other manner along the circumferential element. Notches can also be used with conventional circumferential elements that do not include the corrugated pattern, such as a scaffold depicted in FIG. 1.

The scaffold may further comprise at least one radiopaque marker, which can be accommodated in the marker dots as described herein. The radiopaque markers may assume a variety of different sizes and shapes. The radiopaque marker may be electron-dense or x-ray refractile markers, such as metal particles or salts. Non-limiting examples of suitable marker metals include iron, gold, colloidal silver, zinc and magnesium, either in pure form or as organic compounds. Other radiopaque materials are tantalum, tungsten, platinum/iridium, or platinum. Heavy metal and heavy earth elements are useful in variety of compounds such as ferrous salts, organic iodine substances, bismuth or barium salts, etc. Further embodiments that may be utilized may encompass natural encapsulated iron particles such as ferritin that may be further cross-linked by cross-linking agents. Ferritin gel can be constituted by cross-linking with low concentrations (0.1-2%) of glutaraldehyde. The radiopaque marker may be constituted with a binding agent of one or more biodegradable polymer, such as PLLA, PDLA, PLGA, PEG, etc. In one embodiment comprising a radiopaque marker, iron containing compounds or iron particles are encapsulated in a PLLA polymer matrix to produce a pasty substance, which can be injected or otherwise deposited in the hollow receptacle contained about the stent. In another embodiment, the marker can be made from a biodegradable or bioabsorbable material.

The scaffolds may also have a transition zone between the end zone and the main body. The transition zone may be formed from a plurality of undulations, each undulation comprising two adjacent connection elements connected by a loop with the width of the loop varying across the transition zone. The transition zone may comprise a plurality of polygons where the surface area of adjacent polygons in the transition zone increases circumferentially. U.S. Patent Publication No. 20110125251. The transition zone may take other suitable configurations.

The dimensions of the scaffold may vary from about 10 mm to about 300 mm in length, from 20 mm to about 300 mm in length, from about 40 mm to about 300 mm in length, from about 20 mm to about 200 mm in length, from about 60 mm to about 150 mm in length, or from about 80 mm to about 120 mm in length. The internal diameter (I.D.) of the stent may range from about 2 mm to about 25 mm, from about 2 mm to about 5 mm (e.g., for the coronary arteries), from about 4 mm to about 8 mm (e.g., for neurological spaces in the CNS, both vascular and nonvascular), from about 6 mm to about 12 mm (e.g., for the iliofemoral), from about 10 mm to about 20 mm (e.g., for the ilioaortic) and from about 10 mm to about 25 mm (e.g., for the aortic).

The device of the present invention may be used as a self-expanding stent or with any balloon catheter stent delivery system, including balloon catheter stent delivery systems described in U.S. Pat. Nos. 6,168,617, 6,222,097, 6,331,186 and 6,478,814. In one embodiment, the present device is used with the balloon catheter system disclosed in U.S. Pat. No. 7,169,162.

The scaffold of the present invention may be used with any suitable catheter, the diameter of which may range from about 0.8 mm to about 5.5 mm, from about 1.0 mm to about 4.5 mm, from about 1.2 mm to about 2.2 mm, or from about 1.8 to about 3 mm. In one embodiment, the catheter is about 6 French (2 mm) in diameter. In another embodiment, the catheter is about 5 French (1.7 mm) diameter.

The scaffold may be inserted into the lumen of any vessel or body cavity expanding its cross-sectional lumen. The invention may be deployed in any artery, vein, duct or other vessel such as a ureter or urethra and may be used to treat narrowing or stenosis of any artery, including, the coronary, infrainguinal, aortoiliac, subclavian, mesenteric or renal arteries. Other types of vessel obstructions, such as those resulting from a dissecting aneurysm are also encompassed by the invention. The subjects that can be treated using the scaffolds and methods of this invention are mammals, including a human, horse, dog, cat, pig, rabbit, rodent, monkey and the like.

The scaffold of the present invention may be formed from at least one bioabsorbable polymer representing a wide range of different polymers which is capable of crystallizing. Typically, bioabsorbable polymers comprise aliphatic polyesters based on lactide backbone such as poly L-lactide (PLLA), poly D-lactide (PDLA), poly D,L-lactide, meso-lactide, glycolides, lactones, as homopolymers or copolymers, as well as formed in copolymer moieties with co-monomers such as, trimethylene carbonate (TMC) or ε-caprolactone (ECL). U.S. Pat. Nos. 6,706,854 and 6,607,548; EP 0401844; and Jeon et al. *Synthesis and Characterization of Poly (L-lactide)-Poly(ε-caprolactone)*. Multiblock Copolymers Macromolecules 2003: 36, 5585-5592. The copolymers comprises a moiety such as L-lactide or D-lactide of sufficient length that the copolymer can crystallize and not be sterically hindered by the presence of glycolide, polyethylene glycol (PEG), ε-caprolactone, trimethylene carbonate or monomethoxy-terminated PEG (PEG-MME). For example, in certain embodiments greater than 10, 100 or 250 L or D-lactides may be arrayed sequentially in the polymer. The stent may also be composed of bioabsorbable polymeric compositions such as those disclosed in U.S. Pat. Nos. 7,846,361; 7,897,224 and 8,137,603; and applicant's co-pending U.S. Patent Publication No. 2010/0093946.

Based on the presence of the monomer type, the following polymer nomenclature can be used.

| | |
|---|---|
| LPLA: | Poly(L-lactide) |
| LPLA-PEG: | Poly(poly-L-lactide-polyethylene glycol) |
| DPLA: | Poly(D-lactide) |
| DPLA-TMC: | Poly(poly D-lactide-co-trimethylene carbonate) |
| DLPLA: | Poly(DL-lactide), a racemic copolymer D-co-L-lactide |
| LDPLA: | poly(L-co-D-lactide) |
| LDLPLA: | Poly(L-co-DL-lactide), named for the method of monomer introduction |
| PGA: | Poly(glycolide) |
| PDO: | Poly(dioxanone) (PDS is Trademark) |
| SR: | "Self reinforced" (a processing technique) |
| TMC: | Trimethylene carbonate |
| PCL: | Poly(ε-caprolactone) |
| LPLA-TMC: | Poly(poly L-lactide-co-trimethylene carbonate) |
| LPLG: | Poly(L-lactide-co-glycolide) |
| POE: | Poly Orthoester |

In an embodiment of the present invention, the composition comprises a base polymer of poly(L-lactide) or poly (D-lactide). Other base polymer compositions include blends of poly(L-lactide) and poly(D-lactide). Other advantageous base polymer compositions include poly(L-lactide-co-D,L-lactide) or poly(D-lactide-co-D,L-lactide) with a D,L-lactide co-monomer molar ratio from 10 to 30%, and poly(L-lactide-co-glycolide) or poly(D-lactide-co-glycolide) with a glycolide co-monomer molar ratio from 10 to 20%.

Another embodiment embodies a base polymer featuring a poly(L-lactide) moiety, and/or a poly(D-lactide) moiety, linked with a modifying copolymer thereof, including poly (L-lactide-co-tri-methylene-carbonate or poly(D-lactide-co-tri-methylene-carbonate) and (L-lactide-co-ε-caprolactone), or poly(D-lactide-co-εaprolactone), in the form of block copolymers or blocky random copolymers, wherein the lactide chain length is sufficient to effect cross-moiety crystallization. Cross moiety crystallization of compositions with copolymers affords increased modulus data in tensile tests avoiding the method for reducing the tensile strength in the polymer blend.

The polymer composition can allow for the development of the lactide racemate (stereo complex) crystal structure, between the L and D moieties, to further enhance the mechanical properties of the bioabsorbable polymer medical device. The formation of the racemate (stereo complex) crystal structure can accrue from formulations such as combinations of:

Poly L-lactide with Poly D-lactide with Poly L-lactide-co-TMC;
Poly D-lactide with Poly L-lactide-co-TMC;
Poly L-lactide with Poly D-lactide-co-TMC;
Poly L-lactide with Poly D-lactide with Poly D-lactide-co-TMC;
Poly L-lactide-co-PEG with Poly D-lactide-co-TMC; and
Poly D-lactide-co-PEG with Poly L-lactide-co-TMC.

Poly-lactide racemate compositions can be "cold formable or bendable" without adding additional heat. Cold-bendable scaffolds of the invention do not require heating to become flexible enough to be crimped onto a carrier device or accommodate an irregularly shaped organ spaces. Cold bendable ambient temperatures are defined as room temperature not exceeding 30° C. Cold-bendable scaffolds can afford sufficient flexibility when implanted allowing for an expanded scaffold device in an organ space such as pulsating vascular lumen. For example, in terms of a stent, it may be desirable to utilize polymeric compositions that afford mostly amorphous polymer moieties after fabrication that can crystallize particularly when the secondary nested or end-positioned meandering connection elements when the scaffold is strained by stretching upon balloon expansion for implantation. Such cold-bendable polymeric scaffold embodiments of are not brittle and do not have to be preheated to a flexible state prior to implantation onto a contoured surface space in the body. Cold-bendability allows these blends to be crimped at room temperature without crazing, and moreover, the blends can be expanded at physiological conditions without crazing.

Poly-lactide racemate compositions and non-racemate compositions of embodiments herein may be processed to have blocky moieties allowing cross moiety crystallization even with the addition of an impact modifier to the blend composition. Such a blend introduces the possibility to design device specific polymer compositions or blends by producing either single or double Tg's (glass melt transition points).

As is understood in this art, polymer compositions of the present invention can be customized to accommodate various requirements of the selected medical device. The requirements include mechanical strength, elasticity, flexibility, resilience, and rate of degradation under physiological and localized anatomical conditions. Additional effects of a specific composition concern solubility of metabolites, hydrophilicity and uptake of water and any release rates of matrix attached or enclosed pharmaceuticals.

The polymer implant utility can be evaluated by measuring mass loss, decrease in molecular weight, retention of mechanical properties, and/or tissue reaction. More critical for scaffold performance are hydrolytic stability, thermal transitions crystallinity and orientation. Other determinants negatively affecting scaffold performance include, but not exclusively, monomeric impurities, cyclic and acyclic oligomers, structural defects and aging.

The scaffold fashioned from the polymer compositions above may be significantly amorphous post extrusion or molding. The scaffold may be subjected to controlled re-crystallization to induce incremental amounts of crystallinity and mechanical strength enhancement. Further crystallization can be induced by strain introduction at the time of device deployment. Such incremental re-crystallization may be employed either on a scaffold "blank" prior to secondary or final fabrication (such as by laser cutting) or post such secondary fabrication. Crystallization (and thus mechanical properties) can also be maximized by strain induction such as by "cold" drawing polymeric tubing, hollow fiber, sheet or film, or monofilament prior to further fabrication. Crystallinity has been observed to contribute a greater stiffness in the scaffold. Therefore, the polymer composition and steric complex of the scaffold has both amorphous and paracrystalline moieties. The initially semicrystalline polymer portion can be manipulated by the action of stretching or expansion of a given device. Yet an adequate amount of amorphous polymeric character is desirable for flexibility and elasticity of the polymeric device. The usual monomer components include lactide, glycolide, caprolactone, dioxanone, and trimethylene carbonate. The scaffold may also be constructed to allow relatively uniform exposure to local tissue or circulatory bioactive factors and enzymes perfusing and acting on the polymer structure during bioabsorption.

The rate of in situ breakdown kinetics of the polymeric matrix of an organ space implant, such as a cardiovascular stent, is sufficiently gradual to avoid tissue overload, inflammatory reactions or other more adverse consequences. In an embodiment, the scaffold is fabricated to survive at least 1, 2, 3, 4, 5, 6, 7, 8, 9, 10, 11, 12, 24 or 36 months.

Pharmaceutical compositions may be incorporated within the polymers by, for example, grafting to the polymer active sites, or coating. An embodiment of the polymer according to the invention affords attachment or incorporation the biological healing factors or other drugs in the polymeric matrix or a polymer coating.

In another embodiment, the composition may be constructed to structurally enclose or attach to drugs in the polymeric matrix. The purpose of such additives may to provide, for example with respect to a stent, treatment of the cardiovascular system or in vascular site in contact with the medical device polymer. The kind of enclosure or attachment of drugs in the polymer may determine the rate of release form the scaffold. For example, the drug or other additive may be bound in the polymer matrix by various known methods including but not limited to covalent bonds, non-polar bonds as well as an ester or similar bioreversible bonding means.

In one embodiment, a bioabsorbable implantable medical device may be covered with a biodegradable and bioabsorbable coating containing one or more barrier layers where the polymer matrix contains one or more of the aforementioned pharmaceutical substances. In this embodiment, the barrier layer may comprise a suitable biodegradable material, including but not limited to, suitable biodegradable polymers including: polyesters such as PLA, PGA, PLGA, PPF, PCL, PCC, TMC and any copolymer of these; polycarboxylic acid, polyanhydrides including maleic anhydride polymers; polyorthoesters; poly-amino acids; polyethylene oxide; polyphosphacenes; polylactic acid, polyglycolic acid and copolymers and mixtures thereof such as poly(L-lactic acid) (PLLA), poly(D,L-lactide), poly(lactic acid-co-glycolic acid), 50/50 (DL-lactide-co-glycolide); polydixanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate. The number of barrier layers that the polymeric scaffold on a device may have depends on the amount of therapeutic need as dictated by the therapy required by the patient. For example, the longer the treatment, the more therapeutic substance required over a period of time, the more barrier layers to provide the pharmaceutical substance in a timely manner.

In another embodiment, the additive in the polymer composition may be in the form of a multiple component pharmaceutical composition within the matrix such as containing a last release pharmaceutical agent to retard early neointimal hyperplasia/smooth muscle cell migration and proliferation, and a secondary biostable matrix that releases a long acting agent for maintaining vessel patency or a positive blood vessel remodeling agent, such as endothelial nitric oxide synthase (eNOS), nitric oxide donors and derivatives such as aspirin or derivatives thereof, nitric oxide producing hydrogels, PPAR agonist such as PPAR-α gands, tissue plasminogen activator, statins such as atorvastatin, erythropoietin, darbepotin, serine proteinase-1 (SERP-1) and pravastatin, steroids, and/or antibiotics.

Pharmaceutical compositions may be incorporated into the polymers or may be coated on the surface of the polymers after mixing and extrusion by spraying, dipping or painting or microencapsulated and then blended into the polymer mixture. U.S. Pat. No. 6,020,385. If the pharmaceutical compositions are covalently bound to the polymer blend, they may be linked by hetero- or homo-bifunctional cross linking agents (see, http://www.piercenet.com/products/browse.cfm?fldID=020306).

Pharmaceutical agents that may be incorporated into the scaffolds or may be coated on the scaffolds include, but are not limited to, (i) pharmacological agents such as, (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, thymidine kinase inhibitors, rapamycin, 40-0-(2-Hydroxyethyl)rapamycin (everolimus), 40-0-Benzyl-rapamycin, 40-0(4'-Hydroxymethyl)benzyl-rapamycin, 40-0-[4'-(1,2-Dihydroxyethyl)]benzyl-rapamycin, 40-Allyl-rapamycin, 40-0-[3'-(2,2-Dimethyl-1,3-dioxolan-4(S)-yl-prop-2'-en-1'-yl]-20 rapamycin, (2':E,4'S)-40-0-(4',5'.: Dihydroxypent-2'-en-1'-yl), rapamycin 40-0(2Hydroxy) ethoxycar-bonylmethyl-rapamycin, 40-0-(3-Hydroxypropyl-rapamycin 40-0-((Hydroxy)hexyl-rapamycin 40-0-[2-

(2-Hydroxyl)ethoxy]ethyl-rapamycin, 40-0-[(3S)-2,2Dimethyldioxolan-3-yl]methyl-rapamycin, 40-0-[(2S)-2,3-Dihydroxyprop-1-yl]-rapamycin, 40-0-(2-Acctoxy)ethyl-rapamycin, 40-0-(2-Nicotinoyloxy)ethyl-rapamycin, 40-0-[2-(N-25 Morpholino) acetoxyethyl-rapamycin, 40-0-(2-N-Imidazolylacetoxy)ethyl-rapamycin, 40-0[2-(N-Methyl-N'-piperazinyl)acetoxy]ethyl-rapamycin, 39-0-Desmethyl-3.9, 40-0,0 ethylene-rapamycin, (26R)-26-Dihydro-40-0-(2-hydroxyl)ethyl-rapamycin, 28-0 Methyrapamycin, 40-0-(2-Aminoethyl)-rapamycin, 40-0-(2-Acetaminoethyl)-rapamycin 40-0(2-Nicotinamidoethyl)-rapamycin, 40-0-(2-(N-Methyl-imidazo-2' ylcarbcthoxamido)ethyl)-30 rapamycin, 40-0-(2-Ethoxycarbonylaminoethyl)-rapamycin, 40-0-(2-Tolylsulfonamidoethyl)-rapamycin, 40-0-[2-(4',5'-Dicarboethoxy-1',2';3'-triazol-1'-yl)-ethyl]rapamycin, 42-Epi-(telrazolyl)rapamycin (tacrolimus), and 42-[3-hydroxy-2-(hydroxymethyl)-2-methylpropanoate]rapamycin (temsirolimus) (WO2008/086369); (d) anesthetic agents such as lidocaine, bupivacaine and ropivacaine; (e) anticoagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and, (o) agents that interfere with endogenous vasoactive mechanisms, (ii) genetic therapeutic agents include anti-sense DNA and RNA as well as DNA coding for (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor a and P, platelet-derived endothelial growth factor, platelet-derived growth factor, tumor necrosis factor a, hepatocyte growth factor and insulin-like growth factor, (d) cell cycle inhibitors including CD inhibitors, and (e) thymidine kinase ("TK") and other agents useful for interfering with cell proliferation.

Other pharmaceutical agents that may be incorporated into the scaffolds include, but are not limited to, acarbosc, antigens, beta-receptor blockers, non-steroidal antiinflammatory drugs (NSAID, cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, cyclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, erythropoietin and erythropoietin derivatives, morphinans, calcium antagonists, irinotecan, modafmil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, ctofibrate, fenofibrate, etofylHne, etoposide, famciclovir, famotidine, felodipine, fenoftbrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, Zolpidem, zoplicone, zotipine and the like. See, e.g., U.S. Pat. Nos. 6,897,205, 6,838,528 and 6,497,729.

The stent may also be coated with at least one type of antibodies. For example, the stent may be coated with antibodies or polymeric matrices which are capable of capturing circulating endothelial cells. U.S. Pat. No. 7,037,772 (see also, U.S. Patent Publications Nos. 20070213801, 200701196422, 20070191932, 20070156232, 20070141107, 20070055367, 20070042017, 20060135476, 20060121012).

The scaffold of the present invention may also be formed from metal such as nickel-titanium (Ni—Ti). A metal composition and process of manufacturing the device is disclosed in U.S. Pat. No. 6,013,854. The super elastic metal for the device is preferably a super elastic alloy. A super elastic alloy is generally called "a shape-memory alloy" and resumes its original shape after being deformed to such a degree that an ordinary metal undergoes permanent deformation. Super elastic alloys useful in the invention include: Elgiloy® and Phynox® spring alloys (Elgiloy® alloy is available from Carpenter Technology Corporation of Reading Pa.; Phynox® alloy is available from Metal Imphy of Imphy, France), 316 stainless steel and MP35N alloy which are available from Carpenter Technology corporation and Latrobe Steel Company of Latrobe, Pa., and superelastic Nitinol nickel-titanium alloy which is available from Shape Memory Applications of Santa Clara, Calif. U.S. Pat. No. 5,891,191.

The scaffold of the present invention may be manufactured in numerous ways. The device may be formed from a tube by removing various portions of the tube's wall to form the patterns described herein. The resulting device will thus be formed from a single contiguous piece of material, eliminating the need for connecting various segments together. Material from the tube wall may be removed using various techniques including laser (YAG laser for example), electrical discharge, chemical etching, metal cutting, a combination of these techniques, or other well known techniques. U.S. Pat. Nos. 5,879,381 and 6,117,165 which are hereby incorporated in their entirety by reference. Forming stents in this manner allows for creation of a substantially stress-free structure. In particular, the length may be adapted to that of the diseased part of the lumen in which the stent is to be placed. This may avoid using separate stents to cover the total diseased area.

In an alternate embodiment, a method for fabricating a tube-shaped stent comprising: preparing a racemic poly-lactide mixture; fabricating a biodegradable polymer tube of the racemic poly-lactide mixture; laser cutting the tube until such scaffold is formed. In this embodiment, the fabrication of the scaffold can be performed using a molding technique, which is substantially solvent-free, or an extrusion technique.

Reference is also made, and thereby incorporated in their entirety into this application, to U.S. Pat. Nos. 7,329,277, 7,169,175, 7,846,197, 7,846,361, 7,833,260, 6,0254,688, 6,254,631, 6,132,461, 6,821,292, 6,245,103 and 7,279,005. In addition, U.S. patent application Ser. Nos. 11/781,230, 12/507,663, 12/508,442, 12/986,862, 11/781,233, 12/434,596, 11/875,887, 12/464,042, 12/576,965, 12/578,432, 11/875,892, 11/781,229, 11/781,353, 11/781,232, 11/781,234, 12/603,279, 12/779,767 and 11/454,968, as well as U.S. Patent Publication No. 2001/0029397, are also incorporated in their entirety.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A bioabsorbable polymeric scaffold for implanting in a body lumen, the scaffold having a compressed state and an expanded state, the scaffold comprising:
   a plurality of circumferential elements each having a plurality of undulations in the form of alternating peaks and valleys, the plurality of circumferential elements forming a generally cylindrical shape having a longitudinal axis,
   wherein at least one of the undulations comprises a corrugated pattern comprising at least six linear segments directly connected in series, each of the at least six linear segments has a length that is substantially the same,
   a plurality of first connection elements connecting a first circumferential element and a second circumferential element, the first and second circumferential elements being longitudinally adjacent, a plurality of second connection elements connecting the second and a third circumferential element, wherein the second and third circumferential elements are longitudinally adjacent, and wherein at least one circumferential element among the first, second and third circumferential elements comprises at least two consecutive undulations each comprising the corrugated pattern and extending circumferentially between two adjacent first connection elements or two adjacent second connection elements that are connected to the at least one circumferential element.

2. The scaffold of claim 1, wherein the corrugated pattern includes seven to 36 linear segments.

3. The scaffold of claim 1, wherein the at least six connected linear segments approximate a period of a sinusoidal wave when the scaffold is in an expanded state.

4. The scaffold of claim 1, wherein the at least one of the circumferential elements comprises a plurality of undulations, each of the plurality of undulations comprising the corrugated pattern.

5. The scaffold of claim 1, wherein each of the plurality of circumferential elements comprises a plurality of undulations, each of plurality of undulations of each circumferential element comprising the corrugated pattern.

6. The scaffold of claim 1, wherein each of the plurality of circumferential elements comprises between 6 and 12 undulations.

7. The scaffold of claim 1, wherein at least one notch is placed at a point along one of the circumferential elements where a first or second connection element and the circumferential element intersect.

8. The scaffold of claim 1, wherein the plurality of first connection elements comprise at least two connection elements.

9. The scaffold of claim 8, wherein the plurality of first connection elements comprise three connection elements.

10. The scaffold of claim 1, wherein each of the first connection elements is linear.

11. The scaffold of claim 1, wherein each of the first connection elements is curvilinear.

12. The scaffold of claim 11, wherein each of the first connection elements comprises an S-shaped segment.

13. The scaffold of claim 1, wherein at least one of the first connection elements contains a marker dot.

14. The scaffold of claim 1, wherein the peaks and valleys of the first circumferential element are substantially in-phase with the peaks and valleys of the second circumferential element, and wherein each of the first connection elements connects a valley of the first circumferential element with a peak of the second circumferential element, the peak being adjacent to a valley of the second circumferential element that is longitudinally aligned with the valley of the first circumferential element.

15. The scaffold of claim 14, wherein the peaks and valleys of the second circumferential element are substantially in-phase with the peaks and valleys of the third circumferential element, and wherein each of the second connection elements connects, on one side, to a peak of the second circumferential element which is connected to the first circumferential element by a first connection element, and on the other side, to a valley of the third circumferential element adjacent to a peak of the third circumferential element that is longitudinally aligned with the peak of the second circumferential element.

16. The scaffold of claim 15, wherein each of the first connection elements comprises an S-shaped segment, and wherein each of the second connection elements is linear.

17. The scaffold of claim 15, wherein each of the first connection elements and each of the second connection elements generally extend in a same circumferential direction.

18. The scaffold of claim 14, wherein the peaks and valleys of the second circumferential element are substantially in-phase with the peaks and valleys of the third circumferential element, and wherein each of the second connection elements connects, on one side, to a valley of the second circumferential element adjacent to the peak of the second circumferential element that is connected to the first circumferential element by a first connection element, and on the other side, to a peak of the third circumferential element which is adjacent to a valley of the third circumferential element being longitudinally aligned with the valley of the second circumferential element, and wherein each of the first connection elements is not longitudinally aligned with any of the second connection elements.

19. The scaffold of claim 18, wherein each of the first connection elements comprises an S-shaped or Z-shaped segment, and wherein each of the second connection elements comprises an S-shaped or Z-shaped segment.

20. The scaffold of claim 1, wherein the peaks and valleys of the first circumferential element are substantially in-phase with the peaks and valleys of the second circumferential element, and wherein each of the first connection elements connects a peak of the first circumferential element with a peak of the second circumferential element that is longitudinally aligned with the peak of the first circumferential element.

21. The scaffold of claim 20, wherein the peaks and valleys of the second circumferential element are substantially in-phase with the peaks and valleys of the third circumferential element, and wherein each of the second connection elements connects, on one side, to a valley of the second circumferential element that is adjacent to the peak connected with the first connection element, and on the other side, to a valley of the third circumferential element being longitudinally aligned with the valley of the second circumferential element.

22. The scaffold of claim 1, wherein each of the first connection elements is linear, and each of the second connection elements is linear.

23. The scaffold of claim 20, wherein the peaks and valleys of the second circumferential element are substantially in-phase with the peaks and valleys of the third circumferential element, and wherein each of the second connection elements connects, on one side, to a peak of the second circumferential element that is adjacent to the peak of the second circumferential element being connected to a first connection element, and on the other side, to a peak of the third circumferential element that is longitudinally aligned with the peak of the second circumferential element.

24. The scaffold of claim 23, wherein each of the first connection elements is linear, and each of the second connection elements is linear.

25. The scaffold of claim 1, wherein the peaks and valleys of the first circumferential element are substantially in-phase with the peaks and valleys of the second circumferential element, and wherein each of the first connection elements connects a peak of the first circumferential element with a valley of the second circumferential element, the valley being adjacent to a peak of the second circumferential element that is longitudinally aligned with the peak of the first circumferential element.

26. The scaffold of claim 25, wherein the peaks and valleys of the second circumferential element are substantially in-phase with the peaks and valleys of the third circumferential element, and wherein each of the second connection elements connects, on one side, to a peak of the second circumferential element adjacent to the valley of the second circumferential element that is connected to the first circumferential element by a first connection element, and on the other side, to a valley of the third circumferential element which is adjacent to a peak of the third circumferential element that is longitudinally aligned with the peak of the second circumferential element, and wherein each of the first connection elements is not longitudinally aligned with any of the second connection elements.

27. The scaffold of claim 1, wherein each of the first connection elements and each of the second connection elements generally extend in a same circumferential direction.

28. The scaffold of claim 1, wherein the plurality of the first connection elements connect the first circumferential element and the second circumferential element at every other peak or valley of the first circumferential element.

29. The scaffold of claim 1, wherein when the scaffold is expanded, the scaffold comprises at least one contiguous spiral pattern that includes at least one of the first connection elements and at least one of the second connection elements, the at least one of the first connection elements and the at least one of the second connection elements both connect the second circumferential element at a same peak or valley.

30. The scaffold of claim 1, wherein the scaffold is expanded, the scaffold comprises at least one contiguous spiral pattern that includes at least one of the first connection elements and at least one of the second connection elements, where the at least one of the first connection elements connects the second circumferential element at a first connection location, the at least one of the second connection elements connects the second circumferential element at a second connection location different from the first connection location, the contiguous spiral pattern further comprising a portion of the second circumferential element between the first connection location and the second connection location.

31. The scaffold of claim 1, wherein at least one of the circumferential elements includes a notch at a location where a connection element and the circumferential element intersect.

32. A bioabsorbable polymeric scaffold for implanting in a body lumen, the scaffold having a compressed state and an expanded state, the scaffold comprising:
 a plurality of circumferential elements each having a plurality of undulations in the form of alternating peaks and valleys, the plurality of circumferential elements forming a generally cylindrical shape having a longitudinal axis,
  wherein at least one of the undulations comprises a corrugated pattern comprising at least six linear segments directly connected in series;
 a plurality of first connection elements connecting a first circumferential element and a second circumferential element, the first and second circumferential elements being longitudinally adjacent; and
 a plurality of second connection elements connecting the second and a third circumferential element, wherein the second and third circumferential elements are longitudinally adjacent, and
  wherein at least one circumferential element among the first, second and third circumferential elements comprises at least eight linear segments directly connected in series and defining one or more undulations having a corrugated pattern and the at least eight linear segments extending circumferentially between two adjacent first connection elements or two adjacent second connection elements that are connected to the at least one circumferential element.

\* \* \* \* \*